United States Patent
Deixler et al.

(10) Patent No.: US 12,284,957 B2
(45) Date of Patent: Apr. 29, 2025

(54) BASELINING CRITERIA FOR RF SENSING IN HORTICULTURE APPLICATION

(71) Applicant: SIGNIFY HOLDING B.V., Eindhoven (NL)

(72) Inventors: Peter Deixler, Arlington, MA (US); Hugo José Krajnc, Eindhoven (NL); Hendrik Stevens, Waalre (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 18/010,484

(22) PCT Filed: Jul. 5, 2021

(86) PCT No.: PCT/EP2021/068449
§ 371 (c)(1),
(2) Date: Dec. 15, 2022

(87) PCT Pub. No.: WO2022/008407
PCT Pub. Date: Jan. 13, 2022

(65) Prior Publication Data
US 2023/0240204 A1    Aug. 3, 2023

Related U.S. Application Data

(60) Provisional application No. 63/048,215, filed on Jul. 6, 2020.

(30) Foreign Application Priority Data

Aug. 24, 2020 (EP) .................. 20192417

(51) Int. Cl.
*A01G 9/14* (2006.01)
*A01G 7/04* (2006.01)
(Continued)

(52) U.S. Cl.
CPC ............. *A01G 9/143* (2013.01); *A01G 7/045* (2013.01); *A01G 9/247* (2013.01); *A01G 9/249* (2019.05);
(Continued)

(58) Field of Classification Search
CPC .......... A01G 9/24; A01G 9/249; G01N 22/00; G01N 33/0098
See application file for complete search history.

(56) References Cited

U.S. PATENT DOCUMENTS 10,597,896 B1 * 3/2020 Hamilton ................ E04H 15/10

FOREIGN PATENT DOCUMENTS

| EP | 3674703 A1 | 7/2020 | |
| WO | 2015006675 A2 | 1/2015 | |
| WO | WO-2019100118 A1 * | 5/2019 | ............. A01B 41/06 |

OTHER PUBLICATIONS

Rafael Aroca et al., "Application of Standard EPC/GEM2 UHF RFID Tags as Soil Moisture Sensors", Proceedings, vol. 1, No. 2, Jan. 1, 2017 (Jan. 1, 2017), p. 10, XP055744444, DOI: 10.339/ecsa-3-S5001.

(Continued)

*Primary Examiner* — Monica L Perry
*Assistant Examiner* — Alanna K Peterson

(57) ABSTRACT

The invention provides a horticulture system (1) comprising a plurality of repeating horticulture system units (100) and a control system (300), wherein: each horticulture system unit (100) comprises (i) a horticulture unit space (110) and (ii) a radio transmission pair (120) arranged to monitor the horticulture unit space (110), wherein the radio transmission pair (120) comprises a radio transmitter and a radio receiver arranged in radio signal receiving relationship; the control system (300) is configured to execute in a unit sensing stage (230) a measurement in at least one of the horticulture unit spaces (110) with the respective radio transmission pair (120); the control system (300) is further configured in an operational mode to: (i) execute a first signal sensing stage (231), wherein the first signal sensing stage (231) comprises the unit sensing stage (230) with a first radio transmission pair (121) related to first horticulture unit space (111) thereby providing a first signal (241) to the control system (300); and (ii) determine a plant-related parameter data based on (a) the first signal (241) and (b) a baseline signal (Continued)

(245), wherein the baseline signal (245) is based on a second signal (242) obtained with an execution of a second signal sensing stage (232), wherein the second signal sensing stage (232) comprises the unit sensing stage (230) with a second radio transmission pair (122) related to a second horticulture unit space (112) thereby providing the second signal (242).

13 Claims, 8 Drawing Sheets

(51) Int. Cl.
*A01G 9/24* (2006.01)
*G01N 22/00* (2006.01)
*G01N 33/00* (2006.01)

(52) U.S. Cl.
CPC ......... *G01N 22/00* (2013.01); *G01N 33/0098* (2013.01)

(56) References Cited

OTHER PUBLICATIONS

Fawwaz T Ulaby et al "Microwave Attenuation Properties of Vegetation Canopies", IEEE Transactions on Geoscience and Remote Sensing, IEEE Service Center, Piscataway, NJ, US, vol. 44, No. 5, Sep. 1, 1985 (Sep. 1, 1985), pp. 746-753, XP011158947, ISSN: 0196-2892.

Stuart O. Nelson et al., "RF Sensing of Grain and Seed Moisture Content", IEEE Sensing Journal, vol. 1, No. 2, pp. 119-126, Aug. 2001.

\* cited by examiner (IV)

(V)

(VI)

(IV)

(V)

(VI)

(I)

(II)

(III)

(I)

(II)

BASELINING CRITERIA FOR RF SENSING IN HORTICULTURE APPLICATION

CROSS-REFERENCE TO PRIOR APPLICATIONS

This application is the U.S. National Phase application under 35 U.S.C. § 371 of International Application No. PCT/EP2021/068449, filed on Jul. 5, 2021, which claims the benefit of European Patent Application No. 20192417.2, filed on Aug. 24, 2020, and U.S. Provisional Patent Application Ser. No. 63/048,215, filed on Jul. 6, 2020. These applications are hereby incorporated by reference herein.

FIELD OF THE INVENTION

The invention relates to a horticulture system as well as to a method for determining plant-related parameter data.

BACKGROUND OF THE INVENTION

Methods for sensing a plant-related parameter are known in the art. WO2015006675A2, for instance, describes a system for a plant parameter detection, including: a plant morphology sensor having a first field of view and configured to record a morphology measurement of a plant portion and an ambient environment adjacent the plant, a plant physiology sensor having a second field of view and configured to record a plant physiology parameter measurement of a plant portion and an ambient environment adjacent the plant, wherein the second field of view overlaps with the first field of view; a support statically coupling the plant morphology sensor to the physiology sensor, and a computing system configured to: identify a plant set of pixels within the physiology measurement based on the morphology measurement; determine physiology values for each pixel of the plant set of pixels; and extract a growth parameter based on the physiology values.

SUMMARY OF THE INVENTION

Horticulture is the branch of agriculture that deals with the art, science, technology, and business of growing plants. It may include the cultivation of medicinal plants, fruits, vegetables, nuts, seeds, herbs, sprouts, mushrooms, algae, seaweeds and non-food plants such as grass, ornamental trees and flowers. Plants use the process of photosynthesis to convert light, $CO_2$ and $H_2O$ into carbohydrates (sugars). These sugars are used to fuel metabolic processes and for biomass formation. This biomass formation may include stem elongation, increase of leaf area, flowering, fruit formation, etc.

The space available for food production may be becoming scarcer. Hence innovation in production methods may be needed to deliver higher yields from smaller footprints, while becoming more sustainable (minimum use of energy and water). Producing food in closed environments such as plant farms is a method to meet these demands. In plant farms (also known as plant factories, vertical farms or city farms), food may be grown in multiple layers, making better use of the available space as compared to outdoor growth or growth in greenhouses. This implies that in plant farms natural sunlight will not be able to reach all plants and a substantial proportion of the light may need to come from artificial lighting. In plant farms, there is a desire for providing a controlled environment suitable for, especially tailored for, the cultivation of plants.

Transporting flowers and plants in horticulture facilities has always been a labor-intensive, yet often highly profitable industry. Due to the shortage of manpower, the industry has scaled up to large operations with a very high degree of automation. The automation and resulting application of conveyor belts not only applies to sorting, packaging and shipping activities; in many cases plants are nowadays also grown on (long) conveyor belts. The pots in which they are grown sometimes stand directly on a conveyor belt or can be placed in special plastic discs.

In particular, there may be a desire to monitor plant growth in the plant farm, and to take growth-related actions to improve growth outcomes with regards to, for example, growth rate, differentiation, or disease/pest prevention, especially in dependence of a determined plant-related parameter.

It was observed that using a high-quality baseline as input for the RF sensing algorithm may contribute to accurately estimating the leaf mass of the horticulture plants. As plants in modern growing facilities are in embodiments no longer static but may move along a conveyor belt, it is challenging to create a high-quality baseline of the moved plant at each new location. As plants in modern growing facilities are in embodiments no longer static but may move in the horticulture system, it may be particularly challenging to track the development of the plants. For example, a detrimental environmental effect may be easily missed as plants do not linger in any particular location. It was also recognized by the inventors that in precision horticulture applications the timing of baselining may be important for RF sensing of leaf mass or fruit mass, or other parameters.

Hence, it is an aspect of the invention to provide an alternative horticulture system and/or an alternative method for determining plant-related parameter data, which preferably further at least partly obviates one or more of above-described drawbacks. The present invention may have as object to overcome or ameliorate at least one of the disadvantages of the prior art, or to provide a useful alternative.

The present invention is defined by the independent and dependent claims.

In an aspect, the invention provides a horticulture system comprising a plurality of horticulture system units for growing plants in growth stages and a control system. The plurality of horticulture systems may, in aspects, be repeating horticulture system units. In embodiments, each horticulture system unit comprises (i) a horticulture unit space comprising a plant at a respective growth stage and (ii) a radio transmission pair arranged to monitor the horticulture unit space with radiofrequency sensing. Especially, the radio transmission pair comprises a radio transmitter and a radio receiver arranged in radio signal receiving relationship. Further, in embodiments the control system is especially configured to execute in a unit sensing stage a measurement in at least one of the horticulture unit spaces with the respective radio transmission pair. Especially, the control system is further configured in an operational mode to: (i) execute a sensing stage and (ii) determine a plant-related parameter data. Especially, the control system is configured in the operational mode to execute a first signal sensing stage, wherein the first signal sensing stage comprises the unit sensing stage with a first radio transmission pair related to first horticulture unit space (especially hosting a plant) of a first horticulture sensing unit thereby providing a (related) first signal to the control system. Especially, the control system is configured in the operational mode to execute a second signal sensing stage, wherein the second signal sensing stage comprises the unit sensing stage with a second radio transmission pair related to a second horticulture unit space of a second horticulture system unit thereby providing a second signal to the control system. Yet further, especially the control system is configured in the operational mode to determine a volumetric plant-related parameter data of the plant in the first horticulture space based on (a) the first signal and (b) a baseline signal. Especially, in embodiments the baseline signal is derived from the second signal obtained with an execution of a second signal sensing stage. Said volumetric plant-related parameter data is selected from the group comprising a leaf volume, a root volume, and a fruit volume.

Hence, in embodiments the invention provides a horticulture system comprising a plurality of horticulture system units for growing plants in growth stages and a control system, wherein: (i) each horticulture system unit comprises (i) a horticulture unit space comprising a plant at a respective growth stage and (ii) a radio transmission pair arranged to monitor the horticulture unit space with radiofrequency sensing, wherein the radio transmission pair comprises a radio transmitter and a radio receiver arranged in radio signal receiving relationship; (ii) the control system is configured to execute in a unit sensing stage a measurement in at least one of the horticulture unit spaces with the respective radio transmission pair; (iii) the control system is further configured in an operational mode to: (I) execute a first signal sensing stage, wherein the first signal sensing stage comprises the unit sensing stage with a first radio transmission pair related to first horticulture unit space (hosting a plant) thereby providing a (related) first signal to the control system; (II) execute a second signal sensing stage, wherein the second signal sensing stage comprises the unit sensing stage with a second radio transmission pair related to a second horticulture unit space of a second horticulture system unit thereby providing a second signal to the control system; and (II) determine a volumetric plant-related parameter data of the plant in the first horticulture space based on (a) the first signal and (b) a baseline signal, wherein the baseline signal is derived from the second signal obtained with an execution of a second signal sensing stage; wherein the volumetric plant-related parameter data is selected from the group comprising a leaf volume, a root volume, and a fruit volume.

With such system, it may be possible to monitor plant development in a reliable way. In particular, the system may facilitate defining a reliable baseline against which a measurement can be compared. It may also be possible to define baselines at different locations. It may also be possible to determine baselines afterwards, such as right afterwards a measurement, still a baseline can for that measurement be measured in another horticulture unit space. Yet further, the present system allows determining a baseline for a moving plant, but also for a moving plant that grows. Hence, with the present invention the baseline may also be updated in time. Hence, the invention allows determining a baseline for an element, such as a plant, in a first horticulture unit space, by determining the baseline in a second unit horticulture space. This provides freedom in time and place, and may also enhance controllability and reliability. Further, the present invention allows using an existing infrastructure to monitor plants in a plant factory. Yet further, the invention allows including microclimate parameters in the baseline.

In particular, existing horticulture infrastructure may typically have a repetitive structure. For example, lighting, heating, and/or watering elements may be arranged in a repetitive pattern. Hence, two or more spatially separated horticulture unit spaces may have (essentially) the same environmental (hardware) parameters, which may direct comparisons between measurements related to these spaces. Environmental hardware parameters refer e.g. to a conveyor belt, a floor, irrigation infrastructure, a lighting infrastructure, etc. Environmental parameters like temperature, humidity, lighting, etc., see below may in embodiments be controllable, and may in specific embodiments individually controlled for different horticulture unit spaces.

As indicated above, the horticulture system may comprise a plurality of repeating horticulture system units. Here, the term "unit" is applied as there may be a repetitive structure of positions for plants and radiation transmission pairs for such positions. For instance, would a plant be positioned at n different positions during a plant growth, e.g. a first position with an empty pot, a second position with a pot filled with substrate, a third position with a pot filled with substrate and a seed or seedling, a fourth position of the pot during a part of the growth period, a fifth position of the pot during a later part of the growth period, and a sixth position of the pot for a harvesting stage; then for each position the associated radio transmission pair may be able to sense the pot etc. in the specific position. Would e.g. the pot in a specific stage sequentially positioned in the different positions during a limited time, such that there is essentially no change, and under identical conditions, the signal of the related radio transmission pairs are assumed to be essentially the same. For instance, these six different positions in this example can all be on the same transport belt. Hence, the term horticulture system units refers to essentially identical parts (or (physical) stages) of a horticulture system.

Hence, each horticulture system unit comprises (i) a horticulture unit space and (ii) a radio transmission pair arranged to monitor the horticulture unit space. Herein, the term "horticulture space" refers to a part in a space wherein the plant at least temporarily can stay. These horticulture spaces may be physically separated parts, such as separated by walls, plates, (plastic) curtains, etc., but may in other embodiments be different parts of the same space, such as a space over a conveyor belt. A set of one or more radio transmission pairs may especially be suited to sense in a specific horticulture space. Hence, a set of one or more radio transmission pairs may be dedicated to a specific horticulture space. Hence, the phrase "related to a horticulture unit space", and similar phrases, may also be interpreted as "for a horticulture unit space", and similar phrases.

It is possible that a single radio transmission pair belongs two sets (of two or more) radio transmission pairs for an adjacent horticulture space. However, based on machine learning, commissioning stages, etc., sets of one or more radio transmission pairs may be used to sense in a specific horticulture space. In embodiments, each horticulture system unit may also comprise a plurality of the radio transmission pairs. Further, in embodiments the radio transmission pair may comprise a radio transmitter and a radio receiver arranged in radio signal receiving relationship, and in specific embodiments the radio transmission pair comprises a radio transmitter and a plurality of radio receivers arranged in radio signal receiving relationship (with the radio transmitter).

The horticulture system may comprise n units. Especially, n is at least 2, such as at least 4, like at least 8 units. However, there may be much more units, such as in the range of 4-1000, or even more. Each horticulture system units comprises a horticulture unit space. Each space may be configured to host a single plant, or a single item of a plant size. However, spaces may also be selected larger, such as configured to host a tray with a plurality of plants. Hence, a space may have the size of 0.5 dm³ up to 500 m³, though other sizes may also be possible. When smaller sizes are chosen, less plants may be measured. Larger size may provide less plant specific information. Hence, in embodiments each horticulture unit space may comprise one or more plant locations.

Before explaining some further aspects in relation to the system, etc., first some attention is paid to horticulture and the use of radio transmission pairs.

There may be a desire to monitor plant growth in the plant farm, and to take growth-related actions to improve growth outcomes with regards to, for example, growth rate, differentiation, or disease/pest prevention, especially in dependence of a determined plant-related parameter.

An even approximate estimation of plant mass, such as the total leaf mass of a plant, may already provide valuable insights to the grower. For example, a leaf mass estimation may be used for detecting deficiencies during the plant's growth phase as well as predicting the yield at harvest. For instance, deviations from expected leaf appearance, plant mass and growth behavior may trigger the grower to inspect a certain area of a horticulture system for disease or for abnormal environmental conditions, or to adjust certain control parameters (for example irrigation or nutrient application).

Plants in horticulture systems may currently be primarily observed manually and/or with camera aid. Manual observations may be cumbersome and time-consuming, whereas camera observations may be restricted to frontal views.

Further, current state-of-the-art plant-monitoring solutions may utilize robots, which may disturb the plants; for instance, horticulture AI-sensing robots are known to damage stems and leaves when physically moving a camera within the leaf canopy.

Hence, there is an unmet need to reliably assess growth of horticulture plants in a noninvasive way. In addition, camera-based image processing can only provide an indication of plant size and the plant's outer shape. Hence, measuring the volume or weight of a plant's leaf canopy before harvesting may be challenging for prior art technologies; for example, multispectral image processing might provide insufficient volumetric information as it may rely on 2D or stereo-camera images. To obtain volumetric insights with prior art technologies, the grower may for instance need to mount a very large number of cameras spread at close distance throughout the whole indoor-farming space, which may be both disruptive for horticulture processes and may be economically prohibitive.

The invention provides the benefit that the plant-related parameter is determined via a radio signal. As a radio signal interacts with an object, herein especially the plant, the radio signal may be affected, such as partially absorbed, diffracted, scattered and reflected. The type and extent of this effect may depend on a variety of factors, including, for example, object material, object shape, object size, radio frequency etc. Hence, by providing a radio signal from the radio transmitter to the radio receiver via a radio path that at least partially passes through a horticulture space, observations may be made with respect to a plant arranged in the horticulture space, i.e., the radio signal may at least partially pass through (or: "travel through") the horticulture space, and observations may be made with respect to a plant arranged in the horticulture space based on changes in the radio signal. In particular, the method of the invention may facilitate sensing volumetric plant-related parameters, such as a leaf volume, a root volume, or a fruit volume.

The prior art may generally consider the interaction between a plant and a radio signal undesirable, as the plant may interfere with radio communication, especially in that plants may act as disturbances in a wireless radio path and cause absorption, blockage and scattering of radio signals. Here, however, the interaction is taken advantage of to provide improved sensing of a plant-related parameter.

In particular, the invention may relate to sensing with radio frequency (RF) to analyze variations in wireless signal strength and/or wireless multipath propagation, especially compared to baselines (see below); RF sensing measurements may be taken during the plant growth with an RF sensing baseline recorded. The RF sensing baseline may preferably relate to a support and substrate without any seed, tulip bulb or seedling in it. The RF sensing baseline may also be recorded before significant growth of the plant has occurred (in the baby plant stage, the RF sensing will be dominated by the horticulture space, especially the horticulture arrangement, such as a support+substrate). By comparing the RF sensing measurement with the (plant-free) baseline, the current (average) density of a leaf canopy in a horticulture space may be determined.

Further, for example, abnormalities such as accidental water leakage from pipes or clogged sprinklers or unwanted condensation on a plant (which may lead to molding of the plant) or even air drafts within a horticulture system, which may "blow dry" the leaves faster after application of water mist may be detected. The RF sensing may, for example, be used to create irrigation heatmaps visualizing to the grower local non-uniformities of the irrigation or ventilation systems in the horticulture system and hence help to facilitate homogeneous growth across the plants.

In embodiments, a radio transmitter and a radio receiver may be arranged such that a radio path between the radio transmitter and the radio receiver passes through at least part of the horticulture space. Especially, the radio receiver may be configured in a radio signal receiving relationship with the radio transmitter, especially along the radio path.

The term "radio transmitter" may herein refer to any device capable of sending a radio signal. The term "radio signal" may herein especially refer to radiation having a frequency selected from a radio frequency range, especially from the range of 0.5-120 GHz. In embodiments, the radio transmitter may be comprised by a (first) radio, i.e., an element capable of both sending and receiving a radio signal.

The term "radio receiver" may herein refer to any device capable of receiving a radio signal and to provide a related receiver signal. In particular, the radio receiver may be configured in a radio signal receiving relationship with the radio transmitter, i.e., the radio receiver may be configured to receive a radio signal transmitted by the radio transmitter. In particular, the radio receiver may be configured for passively receiving the radio signal transmitted by the radio transmitter, i.e. receiving signals from transmitters but without being specifically timed/orchestrated to know exactly when the transmission will take place. In other words, with regards to passive reception, it is not a coordinated sequence where the receiver knows exactly when each device will transmit (potentially as a response to a trigger the receiver sent first); instead, the receiver is listening to any type of commands, and if it receives a message destined to be used for sensing, it may apply a specific action if needed. Further, in embodiments, passive sensing may also refer to the situation where the device receiving a message is not the same device that transmitted it, as opposed to what may happen with radar-based technologies where a single device transmits a signal and determines a parameter based on the received reflection of that signal. In embodiments, the radio receiver may be comprised by a (second) radio.

The term "radio path" (also: "wireless communication path") may herein refer to a path between the radio transmitter and the radio receiver, wherein a radio signal sent by the radio transmitter can travel along the radio path prior to being detected by the radio receiver. As the radio path passes through at least part of the horticulture space, the radio signal as received by the radio receiver may comprise information pertaining to the horticulture space. Given that a radio signal may be reflected by an object, there may also be a plurality of radio paths between the radio transmitter and the radio receiver. In general, in embodiments, there may be a plurality of radio paths between the radio transmitter and the radio receiver. In embodiments, the radio path may especially be an (essentially) straight path between the radio transmitter and the radio receiver.

In embodiments, the radio signal may especially be indicative of a control command arranged for controlling an electrical device. The electrical device may especially be a horticulture device, such as a lighting device, sensor, and/or actuator (see also below). Hence, in embodiments, radio signals already being used for controlling electrical devices in a horticulture environment, especially a horticulture system, (first function) may be used for the RF-based sensing (second function), especially next to the alternative of using dedicated RF signals for the RF-based sensing.

In embodiments, the method may comprise a (unit) sensing stage. The (unit) sensing stage may comprise executing a measurement in at least one of the horticulture unit spaces with the respective radio transmission pair. In particular, the sensing stage may comprise emitting (also "transmitting") a radio signal with a radio transmitter. The sensing stage may further comprise detecting (or: "receiving") the radio signal with the radio receiver and providing a related (receiver) signal, especially a raw and/or processed related receiver signal. The sensing stage may further comprise determining (a value of) the plant-related parameter based on the receiver signal.

The term "related receiver signal" may herein refer to any signal provided by the radio receiver that is related to, especially at least partially based on or derived from, the radio signal as detected by the radio receiver. Hence, the related receiver signal may comprise the raw radio signal (as received). Further, the related receiver signal may comprise a processed radio signal; for example, the related receiver signal may comprise a message parameter extracted from the radio signal (as received).

In embodiments, a determination stage may comprise the execution of a (computational) analysis, especially a computational algorithm, to determine the plant-related parameter based on the receiver signal. The sensing stage may especially comprise determining the plant-related parameter based on (a comparison between) the receiver signal and the radio signal (as sent by the radio transmitter), taking into account the baseline signal. It will be clear to the person skilled in the art that the radio signal will be affected by the plant in a plant-part-specific and wavelength-specific manner, thereby facilitating determining the plant-related parameter.

In specific embodiments, the invention provides a method for sensing a plant-related parameter in a horticulture space, wherein (i) a radio transmitter and a radio receiver are arranged such that a radio path between the radio transmitter and the radio receiver passes through at least part of the horticulture space, and (ii) the radio receiver is configured in a radio signal receiving relationship with the radio transmitter, wherein the method comprises a sensing stage comprising: emitting a radio signal with the radio transmitter; detecting the radio signal with the radio receiver and providing a related receiver signal; and determining the plant-related parameter based on the receiver signal.

The sensing of the plant-related parameter may benefit from sensing from, for example, multiple angles and/or multiple sides. In particular, different radio paths may be more suitable for particular plant-related parameters. A variety of radio paths may thus result in the potential to measure more plant-related parameters, as well as to obtain higher quality measurements, such as for example of a volumetric plant parameter.

Hence, in embodiments, a plurality of radio transmitters and/or radio receivers may be arranged in and/or around the horticulture space. In particular, a plurality of radio transmission pairs may be configured in radio signal receiving relationships, wherein each radio transmission pair comprises a (respective) radio transmitter and a (respective) radio receiver arranged such that a (respective) radio path between the (respective) radio transmitter and the (respective) radio receiver passes through at least part of the horticulture space.

In further embodiments, a plurality of radio transmitters may be arranged in and/or around the plant cultivation space, such as especially in the respective horticulture unit spaces. In such embodiments, the sensing stage may comprise (sequentially) emitting radio signals from radio transmitters of the plurality of radio transmitters, especially (sequentially) emitting radio signals from single radio transmitters of the plurality of radio transmitters. Further, the sensing stage may comprise (continuously) detecting the (sequentially) emitted radio signals with the radio receiver.

In further embodiments, a plurality of radio receivers may be arranged in and/or around the horticulture unit space (also indicated as "horticulture space"). In such embodiments, the sensing stage may comprise (sequentially) emitting radio signals from the radio transmitter, and (continuously) detecting the (sequentially) emitted radio signals with the plurality of radio receivers. In further embodiments, a plurality of radio transmitters and radio receivers may be arranged in and/or around the horticulture space. In yet further embodiments, a plurality of radio communication pairs may be arranged in and/or around the horticulture space, especially wherein each radio communication pair may comprise a (respective) radio transmitter and a (respective) radio receiver. In such embodiments, the sensing stage may comprise (simultaneously) emitting radio signals from radio transmitters of (at least part of) the plurality of radio communication pairs, especially (simultaneously) emitting radio signals from single radio transmitters of the plurality of radio communication pairs. Further, the sensing stage may comprise (continuously) detecting the (simultaneously) emitted radio signals with the (respective) radio receivers. In particular, in further embodiments, a radio may comprise a radio transmitter and a radio receiver, wherein the radio transmitter is configured in a radio signal receiving relationship with a second radio receiver, and wherein the radio receiver is configured in a radio signal receiving relationship with a second radio transmitter, and wherein the radio the sensing stage comprises simultaneously (or: "concurrently") emitting radio signals from the radio transmitter and the second radio transmitter, and detecting the simultaneously emitted radio signals with the second radio receiver and the radio receiver, respectively.

In embodiments, the radio transmitter may be comprised by a first horticulture device (or: "first horticulture element"), and/or the radio receiver may be comprised by a second horticulture device (or: "second horticulture element"). In particular, the radio transmitter and/or the radio receiver may be integrated into horticulture devices (or "elements") that are commonly employed in horticulture systems. For example, in further embodiments, the first (or second) horticulture device may comprise one or more of a horticulture light generating device, a horticulture light control element, especially a wall switch or occupancy sensor, a (horticulture tray) actuator, a sensor, a horticulture temperature control element, a horticulture robot, etc. In further embodiments, the horticulture device may comprise a horticulture light generating device.

In embodiments, the horticulture system may comprise a plurality of horticulture devices, a plurality of radio transmitters, and a plurality of radio receivers, wherein each of (at least part of) the plurality of horticulture devices comprises a (respective) radio transmitter of the plurality of radio transmitters, and wherein each of (at least part of) the plurality of horticulture devices comprises a (respective) radio receiver of the plurality of radio receivers, The integration of the radio transmitter and/or the radio receiver in commonly employed horticulture elements, may provide the benefit that the radio transmitter and/or radio receiver are integrated in elements that are already going to be present in a horticulture system, rather than that additional elements need to be added, for which additional space may otherwise need to be dedicated. Integration of (at least part of) a plurality of radio transmitters and/or of (at least part of) a plurality of radio receivers in horticulture light generating devices may be particularly beneficial, as horticulture light generating devices may generally be spread out across a horticulture space. Especially horticulture light generating devices may be spatially arranged in a (highly) repetitive pattern, which may facilitate analyzing the receiver signal, and which may facilitate extrapolating suitable sensing parameters determined for one radio transmission pair to a second radio transmission pair.

Hence, in further embodiments, a plurality of radio transmitters and radio receivers may be spatially arranged in and/or around the horticulture space according to a repeating pattern.

The plant-related parameter may comprise any parameter relevant for cultivation of the plant (in the horticulture space). Further, the term "plant-related parameter" may also refer to a plurality of plant-related parameters.

In embodiments, the plant-related parameter may comprise a plant volumetric parameter, especially a plant volumetric parameter selected from the group comprising a leaf density, a leaf size, a leaf length, a leaf volume, a stem volume, a root volume, a fruit volume, a seed volume, and a nut volume, especially from the group consisting of a leaf volume, a stem volume, a root volume, a fruit volume, a seed volume, and a nut volume.

In embodiments, the plant-related parameter may be selected from the group comprising a leaf size, a plant temperature, a plant leaf temperature, a plant root temperature, a plant stem length, a plant fruit size, etc.

In further embodiments, the plant-related parameter may comprise a growth-related parameter, especially a growth-related parameter selected from the group comprising an air-related parameter, a substrate-related parameter, a leaf volume and a weed volume. For example, the growth-related parameter may comprise a weed volume, wherein the weed volume may especially refer to the volume of a second unwanted plant negatively affecting the growth of the plant, particularly wherein the second unwanted plant may use the desired first plant as a means of vertical support to reach higher areas on the plant canopy with more light (similar to a liana on a tree).

As will be clear to the person skilled in the art, the different categories of plant-related parameters are not necessarily mutually exclusive. For example, the leaf volume of a plant may be both a plant volumetric parameter and a growth-related parameter, as the leaves may perform photosynthesis, and may thereby contribute to plant growth.

In embodiments, the horticulture space may comprise a substrate. The term "substrate" may herein especially refer to a surface or material on which a plant lives, growth, and/or obtains its nutrients from. The substrate may especially at least partially surround the roots of the plant. In further embodiments, the substrate may comprise soil. In further embodiments, the substrate may comprise rockwool.

In further embodiments, the radio path may pass through at least part of the substrate, wherein the plant-related parameter comprises a substrate-related parameter selected from the group comprising a substrate humidity level, a substrate salinity level, a substrate humidity uniformity, a substrate density, a substrate thickness, a foreign object (in the substrate), such as a stone and/or a wood piece and/or another plant and/or an animal, and a substrate nutrient parameter, especially a nitrogen level, or especially a nitrogen level uniformity. As the substrate may provide both support and nutrition to the plant, its state may at least partially determine growth outcomes of the plant. Hence, by sensing the substrate-related parameter with the method of the invention, the substrate can be analyzed (over time) and modified if determined necessary or beneficial. For example, if it is determined that the substrate humidity level is deemed too low (or too high), or if the substrate humidity uniformity is insufficient, this may inform and improve future watering actions.

Interactions between the plant and the radio signal may, among others, depend on the frequency of the radio signal. For example, different radio frequencies may be absorbed by the plant, especially by the plant leaves, at different rates, which may further depend on whether or not the plant is in-leaf. Similarly, fruit may, generally, have different dimensions than leaves and may thus predominantly affect different radio frequencies than the plant leaves. Yet further, the radio signal may have positive and/or negative effects on the plant growth depending on the exposed plant part as well as the radio frequency.

Hence, in embodiments, the radio signal may be selected based on an input parameter, wherein the input parameter is selected from a plant characteristic, a time-dependent parameter, and an environmental parameter. In further embodiments, the radio signal may be selected from the range of 0.5-120 GHz, especially from the range of 0.9-60 GHz. In general, the higher the radio frequency, the more it may be absorbed by the plant. However, the absorption (and other interaction types) may differ, for example, for different plant types, leaf shapes and leaf sizes. In particular, higher frequencies may be impacted more by (smaller) leaves, as the size of the leaves may get in the area of the radio wavelength (a few cm), i.e., if the plant leaves dimensions are comparable to the wavelength of the radio signal, the radio signal may be significantly scattered by the leaves. Essentially, the higher the frequency, the more sensitive the RF signal may be to smaller objects. Specifically, when the wavelength of the RF signal has a length approximately the same or—particularly—smaller than the object, the interaction between the RF signal and the object may be stronger. Hence, by selecting the frequency, the sensitivity to different (parts of a) plant can be determined. For example, in embodiments, a frequency selected from the range of 0.5 GHz-5.0 GHz may be selected to detect fruits and/or (large) leaves. In further embodiments, a frequency selected from the range of 20-120 GHz, especially 25-100 GHz, may be selected to detect plant roots. It will be clear to the person skilled in the art that different frequencies may be suitable to detect same plant parts of different types of plants.

Further, some radio frequencies may negatively affect (a part of) a plant. For example, a radio frequency of about 900 MHz was described to inhibit the root growth of a particular bean by inducing oxidative stress. Hence, the radio frequency may be selected to avoid a negative effect of the radio signal on (a part of) the plant. Hence, in specific embodiments, different parts of the plant may be exposed to different radio frequencies.

Hence, in further embodiments, the method may comprise selecting the radio frequency in dependence of a plant characteristic, especially a plant characteristic selected from the group comprising the plant type, plant growth stage, fruit shape, fruit size leaf shape, and leaf size.

For RSSI sensing scattering (by leaves) may be disadvantageous. Hence in further embodiments, the plant leaves may have an (average) leaf dimension $d_L$, wherein the method may comprise selecting the radio frequency such that the corresponding radio wavelength is at least 2.0 $d_L$, especially wherein the leaf dimension is a leaf length, or especially wherein the leaf dimension is a leaf width.

For CSI sensing scattering (e.g., by leaves) may be advantageous. Hence in further embodiments, the plant leaves may have an (average) leaf dimension $d_L$, wherein the method may comprise selecting the radio frequency such that the corresponding radio wavelength is in the range of 0.5 $d_L$-2.0 $d_L$, especially wherein the leaf dimension is a leaf length, or especially wherein the leaf dimension is a leaf width. For example, in embodiments, the corresponding wavelength may be selected from the range of 1 mm-20 cm. A wavelength of about 1 mm may, for example, be suitable for pine-like, especially spike-like, leaves, whereas a wavelength of about 20 cm may, for example, be suitable for wide leaves of small trees.

The term "radio signal" may also refer to a plurality of radio signals. Similarly, the term "radio frequency" may refer to a plurality of radio frequencies. In embodiments, the sensing stage may comprise sequentially emitting radio signals with the radio transmitter, especially wherein the sequentially emitted radio signals comprise (one or more) different radio frequencies. For example, during the sensing stage, such as at a specific growth stage of the plant, different radio frequencies may be provided (sequentially) to detect (a plant-related parameter related to) fruit (e.g. tomatoes) and to detect (a plant-related parameter related to) leaves.

In further embodiments, the radio frequency may be selected from one or more of 0.9 GHz, 1.3 GHz, 2.0 GHz, 2.4 GHz, 5 GHz, 11.6 GHz, 60 GHz.

The water in the plants may absorb some frequencies more than others; those frequencies may be most affected by the plants. In particular, some microwave frequencies (in the GHz range) may closely match the rotational frequency of water and can cause the water molecules to rotate, which may result in a strong absorption effect by the plant material. Hence, in embodiments, the radio frequency may be selected to match a rotational frequency of water.

The term "plant type" may herein refer to plants suited to a particular environment, such as a tropical plant, or such as an aquatic plant, but may herein further refer to a particular species (or genus) of a plant, especially a crop.

In particular, the radio frequency may be selected such that the radio signal is strongly affected by the plant-related parameter in view of the plant characteristic. For example, if the plant-related parameter comprises a leaf volume, the radio frequency may be selected in view of the leaf shape and leaf size of the plant, especially an expected leaf shape and leaf size of the plant type in its present growth stage, such that leaves of the plant have a strong and distinguishable effect on the radio signal. Hence, for example, also the fruit shape and/or the fruit size may be considered when selecting a radio signal for sensing a leaf volume in order to select a radio frequency where the leaves provide a distinguishable effect from the fruit.

In further embodiments, the method may comprise selecting the radio frequency in dependence of a pre-determined plant-related parameter, especially of a pre-determined value of a plant-related parameter. In particular, in such embodiment, the radio frequency may be adjusted as the plant grows in order to, for example, compensate for more and/or larger leaves (or fruits).

The radio signal may comprise a narrow-band signal and/or a broad-band signal, especially a broad-band signal. In particular, a broad-band signal may comprise multiple subcarriers, whereas a narrow-band signal comprises a single subcarrier. In embodiments, the broad-band signal may especially comprise a Wi-Fi-signal.

Herein, the term "plant" is used to refer essentially to any species selected from medicinal plants, vegetables, herbs, sprouts, mushrooms, plants bearing nuts, plants bearing seeds, plants bearing flowers, plants bearing fruits, non-food crops such as grass and ornamental trees, etc. The term "plant" herein may especially refer to Archaeplastida. The Archaeplastida are a major group of eukaryotes, comprising the red algae (Rhodophyta), the green algae, and the land plants (including aquatic plants), together with a small group of freshwater unicellular algae called glaucophytes. Hence, in embodiments the plant may be a land plant. In further embodiments the plant may be an alga (such as one or more of green algae and red algae and unicellular algae called glaucophytes). Further, the term "plant" may herein refer to essentially all stages of plant development. The term "plant" may especially refer to a plurality of (different) plants.

The term "plant part" may herein especially refer to a part of a plant, such as a root, stem, leaf, fruit (if any), flower (if any), nut (if any) etc. Further, the term "plant part" may especially refer to a plurality of (different) plant parts.

The plant-related parameter may comprise any parameter related to a plant, especially a plant volumetric parameter, or especially a growth-related parameter, such as an environmental parameter.

The plant may especially be a type of crop. The term "crop" may herein be used to refer to a plant species or variety that is grown to be harvested as e.g. food, livestock fodder, fuel, or for any other economic purpose. The term "crop" may also relate to a plurality of crops. The term "crop" may herein especially refer to food crops (tomatoes, peppers, cucumbers and lettuce), as well as to plants (potentially) bearing such crops, such as a tomato plant, a pepper plant, a cucumber plant, etc. Examples of crop plants are rice, wheat, barley, oats, chickpea, pea, cowpea, lentil, green gram, black gram, soybean, common bean, moth bean, linseed, sesame, khesari, sunhemp, chillies, brinjal, tomato, cucumber, okra, peanut, potato, corn, pearlmillet, rye, alfalfa, radish, cabbage, lettuce, pepper, sunflower, sugarbeet, castor, red clover, white clover, safflower, spinach, onion, garlic, turnip, squash, muskmelon, watermelon, cucumber, pumpkin, kenaf, oilpalm, carrot, coconut, papaya, sugarcane, coffee, cocoa, tea, apple, pears, peaches, cherries, grapes, almond, strawberries, pine apple, banana, cashew, irish, cassava, taro, rubber, sorghum, cotton, triticale, pigeonpea, and tobacco.

The horticulture unit space (or: "plant cultivation space") may refer to any space dedicated for hosting a plant, especially in a horticulture setting. The term "horticulture" may herein refer to (intensive) plant cultivation for human use and is very diverse in its activities, incorporating food plants (fruits, vegetables, mushrooms, culinary herbs, including feed) and non-food plants (flowers, trees and shrubs, turf-grass, hops, grapes, medicinal herbs). In particular, the term "horticulture space" may herein refer to any space where growth lighting fixtures (giving artificial light) are used to facilitate plant growth. In the future this could not just be vertical farming or inside a greenhouse, but also in outdoor settings where the artificial lighting complements the daylighting and improves plant growth.

In embodiments, the horticulture space may especially refer to a space comprising one or more of a substrate, air, and water, wherein the horticulture space is configured for hosting a plant. For example, in a vertical farm, a horticulture space may comprise a volume essentially defined by horticulture arrangements, such as trays. Generally, for example, a vertical farm may comprise a plurality of horticulture spaces separated by walkways and/or (layered) horticulture arrangements.

In further embodiments, a broad-band signal, especially 60 GHz Wi-Fi, may be used to monitor leaf movements, for instance to detect unwanted air drafts within the greenhouse.

In embodiments, the radio transmitter and the radio receiver may be arranged at different heights, especially at different heights with respect to the top of the leaf canopy (of the plant), or especially at different heights with respect to a floor in the horticulture space. This may be particularly beneficial with regards to sensing plant-related parameters with regards to the plant canopy. Further, when the radio transmitter and the radio receiver are arranged at different heights, there may be less impact from surrounding radio signals, resulting in a relatively larger contribution of absorption on the measured signal.

In embodiments wherein a plurality of radio transmitter and/or radio receivers are arranged, the plurality of radio transmitter and/or radio receivers may especially be arranged at different heights. Thereby, during the sensing stage, plant-related parameters pertaining to different parts of the plant, especially different heights of the plant canopy, may be determined. For example, the method may comprise determining the average leaf mass per area for different heights within the plant canopy (e.g. top third, middle, bottom third of the plant).

In embodiments, the horticulture space may comprise a predetermined volume for plant growth. Especially, the horticulture space may have a volume selected from the range of 100 $cm^3$-100 $m^3$. If the distance between the radio transmitter and the radio receiver is too small, there may be insufficient effect of the horticulture space on the radio signal, especially, for example, if the plant is a seedling with a small canopy. Further, if the distance is too small, (an antenna of) the radio receiver may become saturated, and no variation may be measured. Similarly, however, if the distance between the radio transmitter and the radio receiver is too big, a signal/noise ratio of the radio signal may be negatively affected. Hence, in embodiments, the (shortest) distance between the radio transmitter and the radio receiver may be selected from the range of 10 cm-10 m, especially from the range of 50 cm-10 m.

The above defined horticulture space may comprise a plurality of the horticulture unit spaces (see also above).

Yet further, the horticulture system comprises a control system. The control system is especially configured to control the radio transmission pairs. However, the control system may also be comprised by a larger control system that controls one or more other devices in the horticulture system or may be configured to control one or more other devices in the horticulture system.

The term "controlling" and similar terms especially refer at least to determining the behavior or supervising the running of an element. Hence, herein "controlling" and similar terms may e.g. refer to imposing behavior to the element (determining the behavior or supervising the running of an element), etc., such as e.g. measuring, displaying, actuating, opening, shifting, changing temperature, etc. Beyond that, the term "controlling" and similar terms may additionally include monitoring. Hence, the term "controlling" and similar terms may include imposing behavior on an element and also imposing behavior on an element and monitoring the element. The controlling of the element can be done with a control system, which may also be indicated as "controller". The control system and the element may thus at least temporarily, or permanently, functionally be coupled. The element may comprise the control system. In embodiments, the control system and element may not be physically coupled. Control can be done via wired and/or wireless control. The term "control system" may also refer to a plurality of different control systems, which especially are functionally coupled, and of which e.g. one control system may be a master control system and one or more others may be slave control systems. A control system may comprise or may be functionally coupled to a user interface.

The control system may also be configured to receive and execute instructions form a remote control. In embodiments, the control system may be controlled via an App on a device, such as a portable device, like a Smartphone or I-phone, a tablet, etc. The device is thus not necessarily coupled to the lighting system, but may be (temporarily) functionally coupled to the lighting system.

Hence, in embodiments the control system may (also) be configured to be controlled by an App on a remote device. In such embodiments the control system of the lighting system may be a slave control system or control in a slave mode. For instance, the lighting system may be identifiable with a code, especially a unique code for the respective lighting system. The control system of the lighting system may be configured to be controlled by an external control system which has access to the lighting system on the basis of knowledge (input by a user interface of with an optical sensor (e.g. QR code reader) of the (unique) code. The lighting system may also comprise means for communicating with other systems or devices, such as on the basis of Bluetooth, WIFI, LiFi, ZigBee, BLE or WiMAX, or another wireless technology.

The system, or apparatus, or device may execute an action in a "mode" or "operation mode" or "mode of operation". Likewise, in a method an action or stage, or step may be executed in a "mode" or "operation mode" or "mode of operation" or "operational mode". The term "mode" may also be indicated as "controlling mode". This does not exclude that the system, or apparatus, or device may also be adapted for providing another controlling mode, or a plurality of other controlling modes. Likewise, this may not exclude that before executing the mode and/or after executing the mode one or more other modes may be executed.

However, in embodiments a control system may be available, that is adapted to provide at least the controlling mode. Would other modes be available, the choice of such modes may especially be executed via a user interface, though other options, like executing a mode in dependence of a sensor signal or a (time) scheme, may also be possible. The operation mode may in embodiments also refer to a system, or apparatus, or device, that can only operate in a single operation mode (i.e. "on", without further tunability).

Hence, in embodiments, the control system may control in dependence of one or more of an input signal of a user interface, a sensor signal (of a sensor), and a timer. The term "timer" may refer to a clock and/or a predetermined time scheme.

The control system is configured to execute in a unit sensing stage a measurement in at least one of the horticulture unit spaces with the respective radio transmission pair. Basically, it is meant that the control system has a kind of basic action or operation, which includes that in relation to at least one of the horticulture unit spaces the control system executes a measurement with the radio transmission pair in relation to the respective horticulture unit spaces. Such execution of an action, which may be controlled by the control system, is herein indicated as unit sensing stage. This term refers on the one hand to a sensing stage in relation to a horticulture unit space, but on the other hand also indicates that this operation or action can be executed at multiple times, in each of the horticulture unit spaces, and may thus be as such also have a kind of repetitive structure (but then on a type of method level).

This action or operation can be used to sense e.g. a plant, or a pot, or a plant with a pot in a horticulture unit stage. This can be done in order to determine a horticulture parameter, or horticulture parameters, or a horticulture parameter as function of time, etc. These are herein also indicated with the general term "plant-related parameter data". However, to obtain a reliable signal, it is useful to compare the signal with a baseline signal. Hence, the method may at least include a sensing stage and a stage wherein the plant-related parameter data is determined on the basis of a signal from the sensing stage compared to a baseline signal. The first stage may be an execution of the above indicated action or operation. The latter, i.e. the baseline determination, may be the result of the execution of the above indicated action or operation, or stored results on the basis of (an earlier) baseline determination. Hence, the baseline may be determined earlier, simultaneously or later.

Hence, especially the control system is further configured in an operational mode to execute a first signal sensing stage, wherein the first signal sensing stage comprises the unit sensing stage with a first radio transmission pair related to first horticulture unit space (hosting e.g. a plant) thereby providing a (related) first signal to the control system. During the sensing stage, the horticulture unit space will in general contain an item selected from a plant support (herein also indicated as plant holder), such as a plant pot or a tray, a plant pot or tray with substrate, a plant pot or tray with substrate and seedling or plant, etc. The target contained in the horticulture unit space may depend upon the stage of growing and/or the position within the horticulture system (or horticulture space). In particular, the horticulture unit space may comprise a plant during the first signal sensing stage.

Dependent upon the target to be measured, the desired baseline may be used. For instance, referring to above non-limiting examples of a plant support, a plant pot, a plant pot with substrate, a plant pot with substrate and seedling or plant, etc., the baseline may be determined in another horticulture space without any of these. However, dependent upon the type of information needed it may e.g. also be possible that (i) another horticulture space with the plant support can be used to determine a baseline for the horticulture space with the a plant pot, (ii) another horticulture space with the plant pot can be used to determine a baseline for the horticulture space with the plant pot with substrate, (iii) another horticulture space with the plant pot with substrate can be used to determine a baseline for the horticulture space with the plant pot with substrate and seedling or plant, etc.

The control system may in embodiments have access to one or more different baselines, and/or may generate one or more different baselines by executing the basic action or operation in relation to (another) horticulture unit space. Generating a baseline may be done before the first signal sensing stage. Alternatively or additionally, generating a baseline may also be done during or after the first sensing stage. This is possible due to the fact that there are a plurality of essentially identical horticulture unit spaces.

Herein, the term "horticulture unit space" is especially used in general for any of the horticulture unit spaces. The term "first horticulture unit space" is herein used to indicate one of the horticulture unit spaces for which the first signal sensing stage is applied, and which in general will contain e.g. a plant support, a plant pot, a plant pot with substrate, a plant pot with substrate and seedling or plant. Instead of the terms "other horticulture unit space" or "other horticulture space", the term "second horticulture unit space" may be applied. The term "second horticulture unit space" is herein used to indicate one of the horticulture unit spaces for which the second signal sensing stage is applied, and which in general will contain e.g. an earlier stage of a plant support, a plant pot, a plant pot with substrate, a plant pot with substrate and seedling or plant, such as a horticulture unit space without a plant support, or a horticulture unit space without a plant pot, or a horticulture unit space without with a plant pot but without substrate, or a horticulture unit space with a plant pot with substrate but without a seedling or a plant, or a horticulture unit space without with a plant pot with substrate with seedling or plant, but in an earlier stage than the (first) horticulture unit space with a plant pot with substrate with a seedling or a plant (in a later growth stage).

Hence, especially the control system is further configured in an operational mode to determine a plant-related parameter data based on (a) the first signal and (b) a baseline signal, wherein the baseline signal is based on a second signal obtained with an execution of a second signal sensing stage, wherein the second signal sensing stage comprises the unit sensing stage with a second radio transmission pair related to a second horticulture unit space thereby providing the (related) second signal. As indicated above, the second signal may be retrieved from a library, to which the control system has access and/or may be based on an execution of the second signal sensing stage before (or during or after) the execution of the first signal sensing stage.

Especially, however, in embodiments the control system is configured to execute in the operational mode the second signal sensing stage (with the second radio transmission pair for the second horticulture unit space), prior to the first signal sensing stage. Especially, this may be executed when the same element, such as a plant, is first available in the second horticulture space, wherein during that phase, wherein the element in that second horticulture space, the baseline signal is generated, and subsequently available in the first horticulture space, wherein during that latter phase, wherein the element is in the first horticulture space, the first signal is generated.

Instead of the term "sensing stage", also the term "sensing phase" or "sensing step" may be applied.

The term "baseline" may refer to a reference value, like e.g. a background noise level, or a sensor signal of an item in an earlier stage (see examples above). The term "baseline" may refer to time dependent data, like a variation over time. The term "baseline" may also refer to different parameters that may be taken into account. For instance, the term "baseline" may refer to two or more baselines determined under different conditions, such as different temperature conditions and/or different humidity conditions, under different lighting conditions, under different irrigation conditions, under different nutrition flow conditions, etc.

The first signal may also contain information from which baseline information can be derived or validated. For instance, spikes, noise, may also be determined from the first signal. In this way, the baseline may be validated with the information that can be derived in embodiments from the first signal. In this way, the combination of first signal and second signal may allow a better definition of the baseline than only on the bases of the second signal. Hence, in embodiments the control system is configured to determine in the operational mode the baseline signal on the basis of both the first signal and the second signal.

As indicated above, the invention may especially be useful when there are a plurality of essentially identical system units having essentially identical radio transmission pairs and essentially identical horticulture unit spaces. Hence, in embodiments, the at least one of the horticulture unit spaces and the second horticulture unit space may have an (essentially) identical configuration of the (respective) radio transmission pair relative to the (respective) horticulture unit space. Further, in specific embodiments each horticulture system unit may have an (essentially) identical configuration of the (respective) radio transmission pair relative to the (respective) horticulture unit space. The horticulture unit space may have a volume for which one or more respective) radio transmission pair are especially suitable to determine a sensor signal. Hence, in embodiments each horticulture system unit may have an (essentially) identical configuration of the (respective) radio transmission pair relative to a (respective) plant support, such as a plant holder, like a plant pot, or a tray, in the horticulture unit space. Especially, during a use of the system a plurality of the horticulture unit space comprise identical plant holders. In embodiments, the plant holder may also comprise a tray with one or more, especially, a plurality of plant pots.

The invention may e.g. be useful in systems wherein plants or seedlings move and may grow substantially during transport with a conveyor belt or similar system in a horticulture plant or other type of plant. Conveyor belt systems are e.g. described in US2020100446, WO2010008335, EP2489256, etc. Hence, in specific embodiments the horticulture system may further comprise a transport element, wherein the transport element is configured to move a plant holder sequentially through a series of the horticulture system units (more especially the horticulture unit spaces). The transport element may e.g. comprise a conveyor belt, but may also comprise another type of robot system, such as using robot arms to move a plant holder from one position to the other. By moving the plant holder from one position to another, the plant holder, and thus in embodiments the plant or seedling, etc., may move from one horticulture unit space to another, and may be sensed by respective radio transmission pairs. Hence, the plant holder may sequentially move through a number of horticulture system units, which is herein indicated as series. The term transport element may also refer to a plurality of different transport elements. The term "series of the horticulture system units" may refer to k system units, wherein k is at least 2, like, 4, but k may also be up to tens or even hundreds or thousands. The k system units may be all available horticulture system units comprised by the system, or may be a subset thereof. Hence, in embodiments k=n (see also above), or k<n.

A plant holder may be a pot, a support, a tray, a (little) flask, robot fingers to hold a plant (e.g. for hydroponics), etc., or anything else that may be used in a transport system to hold a seedling or plant. The plant holder may be transported with a robot arm or a conveyor belt, or other transport element.

For instance, in embodiments the second horticulture unit space may not contain the plant holder (during the second signal sensing stage with the second radio transmission pair for the second horticulture unit space). In the first sensing stage, the plant holder (other than used in the second sensing stage) may be available in the first horticulture space. In an alternative example, in embodiments the second horticulture unit space may contain the plant holder but does not contain a plant (during the second signal sensing stage with the second radio transmission pair for the second horticulture unit space). In the first sensing stage, the plant holder (other than used in the second sensing stage) with plant may be available in the first horticulture space. In yet an alternative example, in embodiments the second horticulture unit space may contain the plant holder but does not contain a seedling (during the second signal sensing stage with the second radio transmission pair for the second horticulture unit space). In the first sensing stage, the plant holder (other than used in the second sensing stage) with plant may be available in the first horticulture space. In yet a further alternative example, also for instance (for another baseline) in embodiments the second horticulture unit space may contain the plant holder but does not contain a seedling or a plant (or substrate) (during the second signal sensing stage with the second radio transmission pair for the second horticulture unit space). In the first sensing stage, the plant holder (other than used in the second sensing stage) with plant may be available in the first horticulture space. Of course, other examples may also be possible.

As indicated above, the baseline may essentially be based on a second horticulture unit space that is in terms of (process) stages earlier than the stage in which the first horticulture unit space is. Hence, when not deriving the baseline signal from a library, or when partially deriving the baseline signal from a library, and at least partially deriving the baseline signal from an execution of the second signal sensing stage, this second signal sensing stage may in general be executed on a horticulture unit space upstream of the first horticulture unit space. Hence, in embodiments the second horticulture unit space is configured upstream of the first horticulture unit space in the series of the horticulture system units. Hence, the plant holder or plant pot in the first horticulture unit space has been or could have been in the second horticulture unit space as was used for the second signal sensing stage. Here, the term "could" is used, as the second signal sensing stage may equally well be executed at the same time as the first signal sensing stage (see also above). Hence, the term "upstream" may refer to the process cycle (e.g. including growth cycle) from essentially plant pot to grown plant, or part of such process cycle, wherein an earlier stage in the cycle is upstream (in time and/or physical position), than a later stage in the process cycle. Especially, the process cycle includes one or more growth stages, or a growth stage and a harvest stage, etc.

Above, it has been indicated that the baseline signal may not only in embodiments refer to a background signal as such, but may also include information in relation to environmental parameters, such as (ambient) temperature, (ambient) humidity, (local) lighting conditions, (local) gas composition, (local) nutrition flow conditions, etc. Hence, in embodiments the control system many further be configured to control an environmental parameter of a plurality of the horticulture spaces, and to execute in the operational mode the second signal sensing stage (with the second radio transmission pair for the second horticulture unit space) while varying the environmental parameter. In this way, the baseline may include baseline information in relation to different conditions. For instance, when determining leaf size, this may depend upon the humidity. Hence, the baseline signal should be a baseline signal in dependence of humidity. In specific embodiments, the environmental parameter is selected from the group comprising a temperature, a substrate humidity, a leaf humidity, a relative humidity, an absolute humidity, an airflow, a density of the horticulture growth medium, and a lighting parameter. For instance, different signals may be obtained when the soil is compact or loosened. For instance, the lighting parameter may refer to one or more of (i) intensity of the light (generated by the lighting system or lighting device or luminaire) and (ii) spectral power distribution of the light (generated by the lighting system or lighting device or luminaire).

To this end, the horticulture system may also comprise one or more sensor to determine plant-related parameter and/or environmental parameters in another way than the radio transmission pair. Especially, the horticulture system may comprise one or more sensors to sense one or more environmental parameters. In specific embodiments, the system may comprise a plurality of sensors, which are configured to locally sense such environmental parameter. In this way, for a subset of the total number of horticulture unit spaces such environmental parameter may be determined.

In specific embodiments, the horticulture system may comprise one or more lighting devices, wherein one or more of (a) the radio transmitters and (b) the radio receivers are integrated in the one or more lighting devices.

In yet further embodiments, the horticulture system comprises an actuator selected from the group comprising a temperature control element, a plant trimmer, a water providing element, a nutrition supply element, a plant treatment supply element, a growth inhibitor supply element, a lighting device, a disinfection device, an insect exposure element, and a harvesting element, wherein the control system controls the actuator, and wherein during the operational mode: the control system operates the actuator in dependence of the (determined value of the) plant-related parameter data. Especially, in embodiments the control system may operate the actuator in relation to the first horticulture unit space). For instance, a lack of or diminished plant growth may also indicate infestation. To this end, e.g. the nutrition supply element and/or the plant treatment supply element may be applied. The term "plant treatment" may in specific embodiment be used for describing pesticides, fungicides etc. A growth inhibitor supply element may e.g. be used to ensure uniform growth of the plants and/or to control plant growth in relation to fruit growth, etc. A disinfection device may e.g. comprise a UV lighting device, or other device, to suppress e.g. powdery mildew, or bud mold on cannabis plants, or other infectants.

Further, as indicated above in embodiments the plant-related parameter data may be volumetric plant-related parameter data selected from the group comprising a leaf volume, a root volume, and a fruit volume. Alternatively or additionally, the plant-related parameter data may be selected from the group consisting of leaf density, stem density, root density, and fruit density. Alternatively or additionally, the plant-related parameter data may be selected from the group consisting of a shape of leaves, a shape of stems, a shape of roots, and a shape of fruits. Alternatively or additionally, the plant-related parameter data may be selected from the group consisting of a dimensions of leaves, dimensions of stems, dimensions of roots, and dimensions of fruits. Alternatively or additionally, the plant-related parameter data may refer to shape and/or dimensions of the entire above-substrate part of the plant.

In yet a further aspect, the invention also provides a method for determining a volumetric plant-related parameter data of a plant in a horticulture system comprising a plurality of repeating horticulture system units and a control system. The volumetric plant-related parameter data is selected from the group comprising of leaf volume, a root volume, and a fruit volume. Especially (a) each horticulture system unit comprises (i) a horticulture unit space and (ii) a radio transmission pair arranged to monitor the horticulture unit space with radio frequency sensing. In embodiments, the radio transmission pair comprises a radio transmitter and a radio receiver arranged in radio signal receiving relationship. Further, especially (b) the control system is configured to execute in a unit sensing stage a measurement in at least one of the horticulture unit spaces with the respective radio transmission pair. In specific embodiments the method may comprise executing a first signal sensing stage and determining plant-related parameter data. In embodiments, the method may comprise (a) executing a first signal sensing stage, wherein the first signal sensing stage comprises the unit sensing stage with a first radio transmission pair related to a first horticulture unit space of a first horticulture sensing unit hosting a plant at a respective growth stage thereby providing a (related) first signal to the control system. Further, the method may comprise executing a second signal sensing stage, wherein the second signal sensing stage comprises the unit sensing stage with a second radio transmission pair related to a second horticulture unit space of a second horticulture sensing unit hosting a plant at a respective growth stage thereby providing a second signal to the control system. Yet further, in embodiments, the method may comprise (b) determining a volumetric plant-related parameter data based on (a) the first signal and (b) a baseline signal, wherein the baseline signal is derived from the second signal obtained with an execution of a second signal sensing stage. Hence, in specific embodiments the invention provides a method for determining plant-related parameter data of a plant in a horticulture system comprising a plurality of repeating horticulture system units and a control system; wherein: (a) each horticulture system unit comprises (i) a horticulture unit space and (ii) a radio transmission pair arranged to monitor the horticulture unit space, wherein the radio transmission pair comprises a radio transmitter and a radio receiver arranged in radio signal receiving relationship; and (b) the control system is configured to execute in a unit sensing stage a measurement in at least one of the horticulture unit spaces with the respective radio transmission pair; and wherein the method comprises in embodiments: (a) executing a first signal sensing stage, wherein the first signal sensing stage comprises the unit sensing stage with a first radio transmission pair for a first horticulture unit space hosting a plant thereby providing a (related) first signal to the control system; and (b) determining a plant-related parameter data based on (a) the first signal and (b) a baseline signal, wherein the baseline signal is based on a second signal obtained with an execution of a second signal sensing stage, wherein the second signal sensing stage comprises the unit sensing stage with a second radio transmission pair related to a second horticulture unit space thereby providing the (related) second signal.

In specific embodiments (of the method), the control system may (thus) be configured to execute in the operational mode the second signal sensing stage (with the second radio transmission pair for the second horticulture unit space); wherein the method further comprises moving a plant holder sequentially through a series of the horticulture system units (including a first horticulture system unit comprising the first horticulture unit space); wherein the second horticulture unit space is configured upstream of the first horticulture unit space in the series of the horticulture system units; and wherein the plant-related parameter data are volumetric plant-related parameter data selected from the group comprising a leaf volume, a root volume, and a fruit volume.

Yet further, in specific embodiments (of the method), wherein the horticulture system comprises one or more lighting devices, wherein one or more of (a) the radio transmitters and (b) the radio receivers are integrated in the one or more lighting devices.

The terms "light" and "radiation" are herein interchangeably used, unless clear from the context that the term "light" only refers to visible light. The terms "light" and "radiation" may thus refer to UV radiation, visible light, and IR radiation. In specific embodiments, especially for lighting applications, the terms "light" and "radiation" refer to (at least) visible light.

Yet further, in specific embodiments the horticulture system comprises an actuator selected from the group comprising a temperature control element, a plant trimmer, a water providing element, a nutrition supply element, a lighting device, a disinfection device, an insect exposure element, and a harvesting element, wherein the control system controls the actuator; and wherein the method further comprises controlling the actuator in dependence of the plant-related parameter data in relation to the first horticulture unit space.

Hence, the actuator may be controlled to execute an action. In specific embodiments, the action may comprise controlling temperature (within part of the horticulture space), especially controlling one or more of a plant temperature, a plant leaf temperature, and a plant root temperature, or especially controlling an (average) temperature in the horticulture space. In further embodiments, the action may comprise plant trimming. In further embodiments, the action may comprise providing water. In further embodiments, the action may comprise providing a crop protection treatment, especially a crop protection treatment against a weed and/or a pest. In further embodiments, the action may comprise providing nutrition, especially fertilizer. In further embodiments, the action may comprise providing light, especially a specific light spectrum, such as providing light comprising one or more wavelengths selected from the range of 400-800 nm, and/or such as providing light comprising a wavelength selected for interaction with a plant phytochrome, and/or especially a specific light intensity. In further embodiments, the action may comprise exposing the plants to insects. In further embodiments, the action may comprise harvesting, especially of fruit, or especially of plant leaves. In further embodiments, the action may comprise providing an air flow, especially providing air conditioning, or especially providing an outside air flow.

In aspects, in a first paragraph, the invention provides a horticulture system comprising a plurality of repeating horticulture system units and a control system, wherein: (i) each horticulture system unit comprises (i) a horticulture unit space and (ii) a radio transmission pair arranged to monitor the horticulture unit space, wherein the radio transmission pair comprises a radio transmitter and a radio receiver arranged in radio signal receiving relationship; (ii) the control system is configured to execute in a unit sensing stage a measurement in at least one of the horticulture unit spaces with the respective radio transmission pair; (iii) the control system is further configured in an operational mode to: (I) execute a first signal sensing stage, wherein the first signal sensing stage comprises the unit sensing stage with a first radio transmission pair related to first horticulture unit space (hosting a plant) thereby providing a (related) first signal to the control system; and (II) determine a plant-related parameter data based on (a) the first signal and (b) a baseline signal, wherein the baseline signal is based on a second signal obtained with an execution of a second signal sensing stage, wherein the second signal sensing stage comprises the unit sensing stage with a second radio transmission pair related to a second horticulture unit space thereby providing the (related) second signal.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE EMBODIMENTS

Figure 1A:
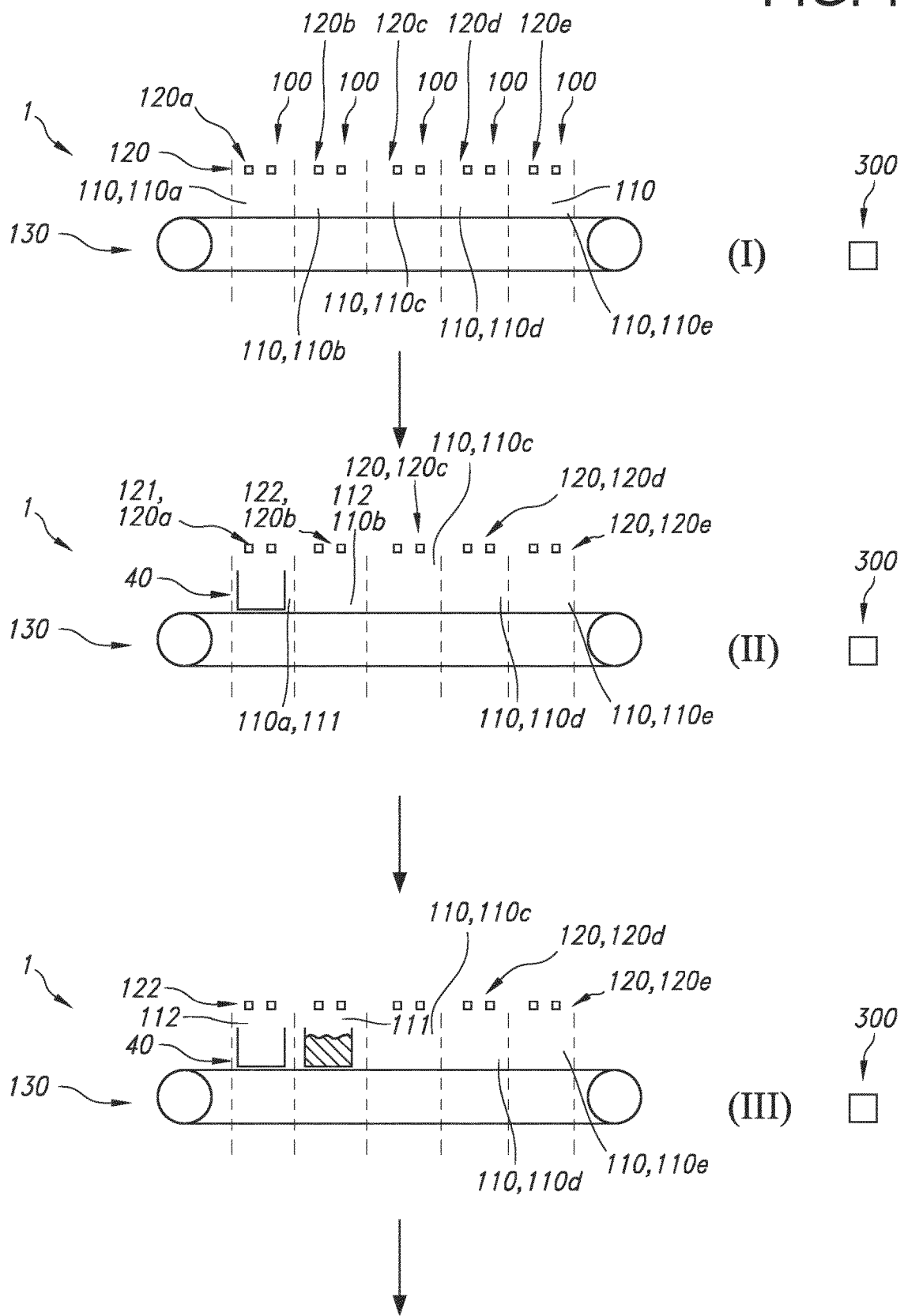
FIGS. 1a-1d schematically depict some aspects of the invention.
Figure 1A:
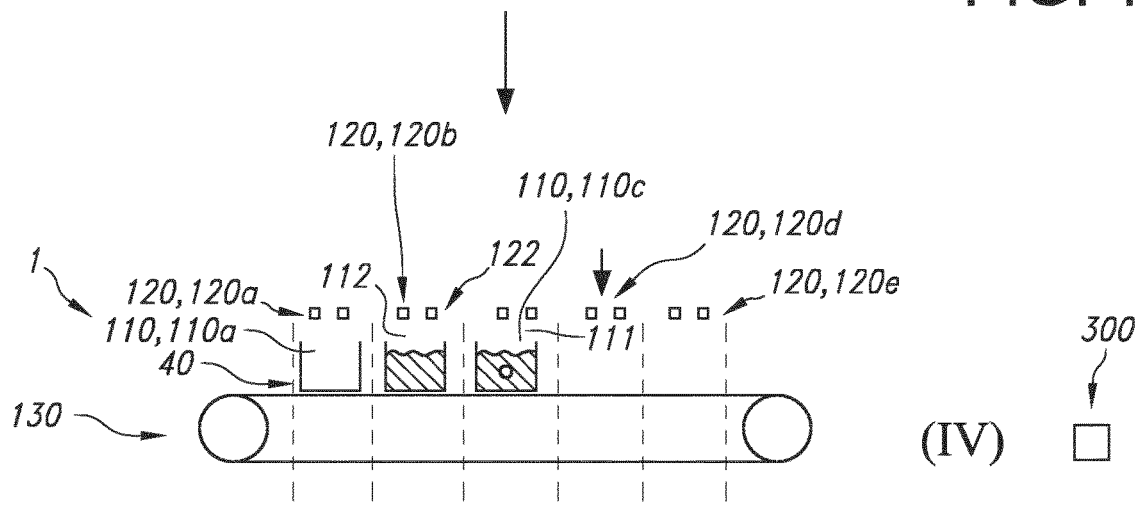
Figure 1A:
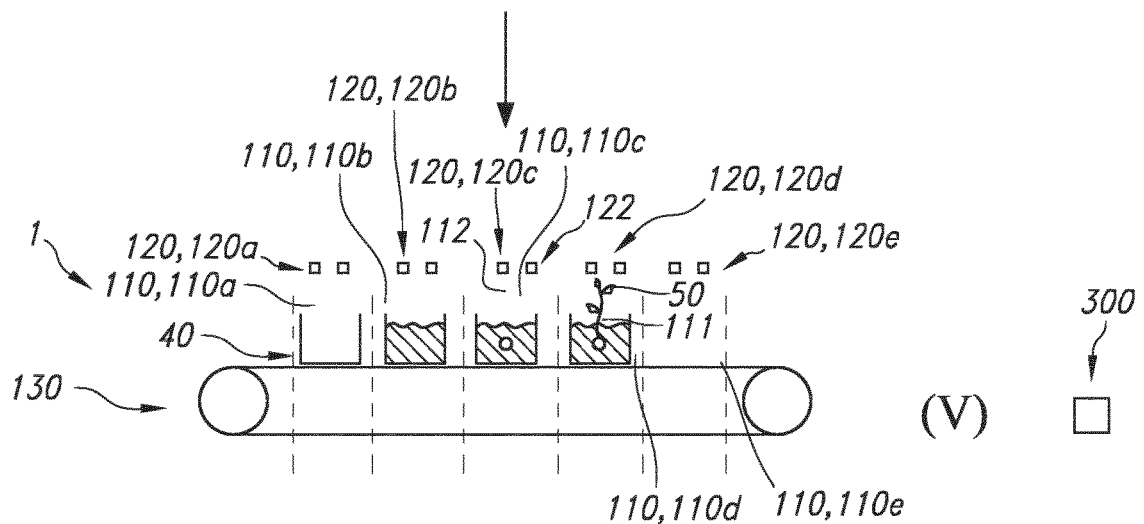
Figure 1A:
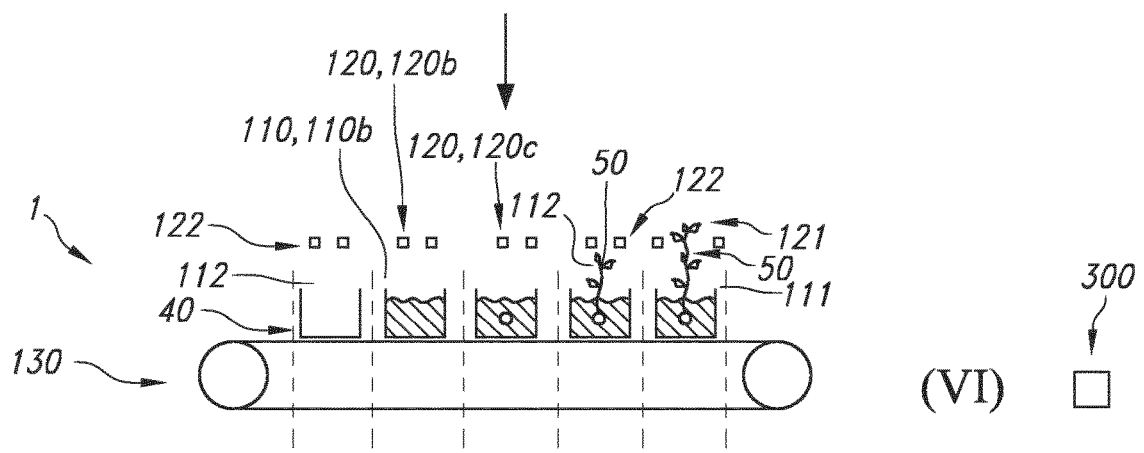
Figure 1B:
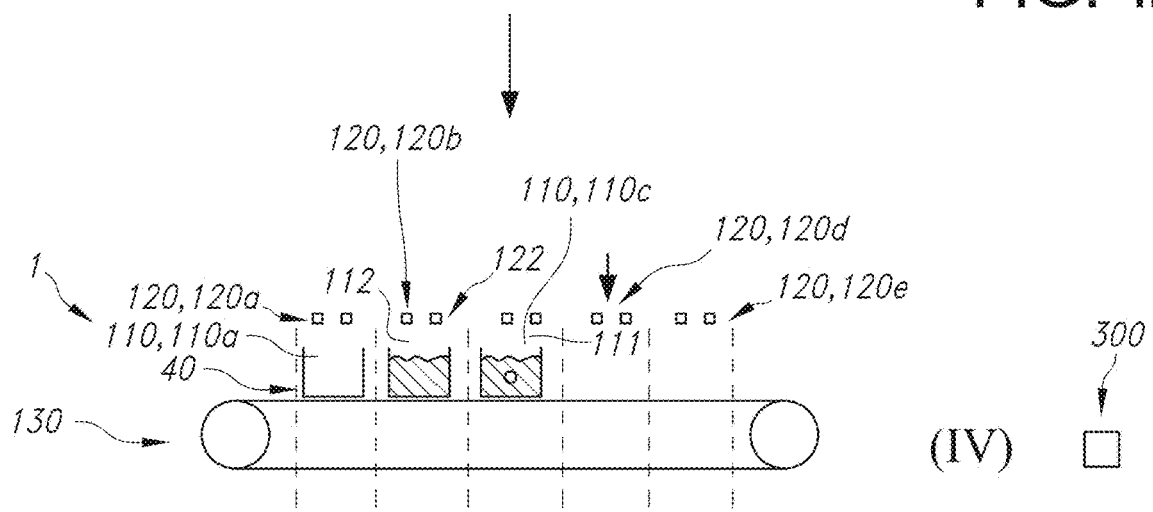
Figure 1B:
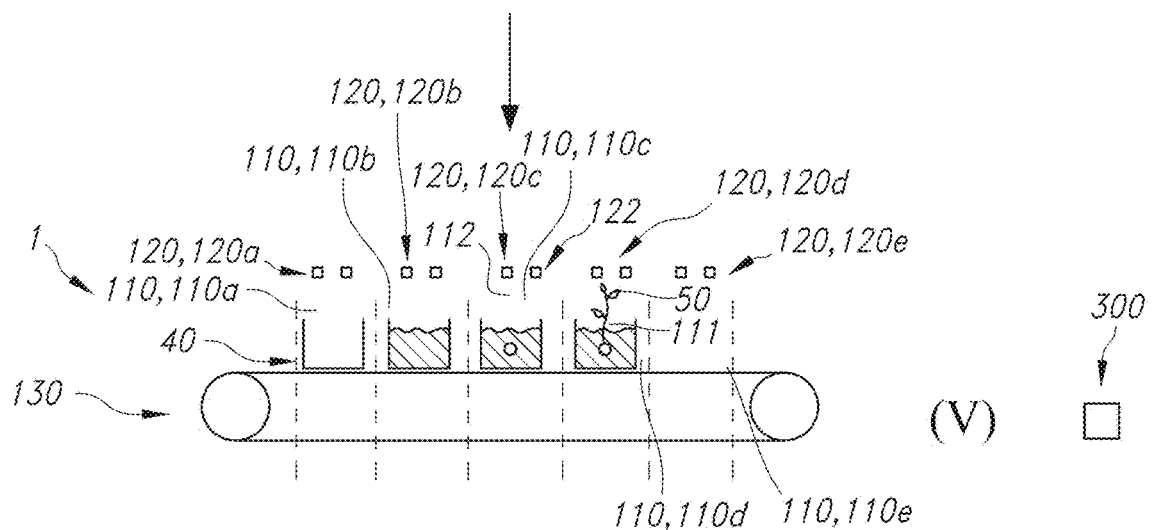
Figure 1B:
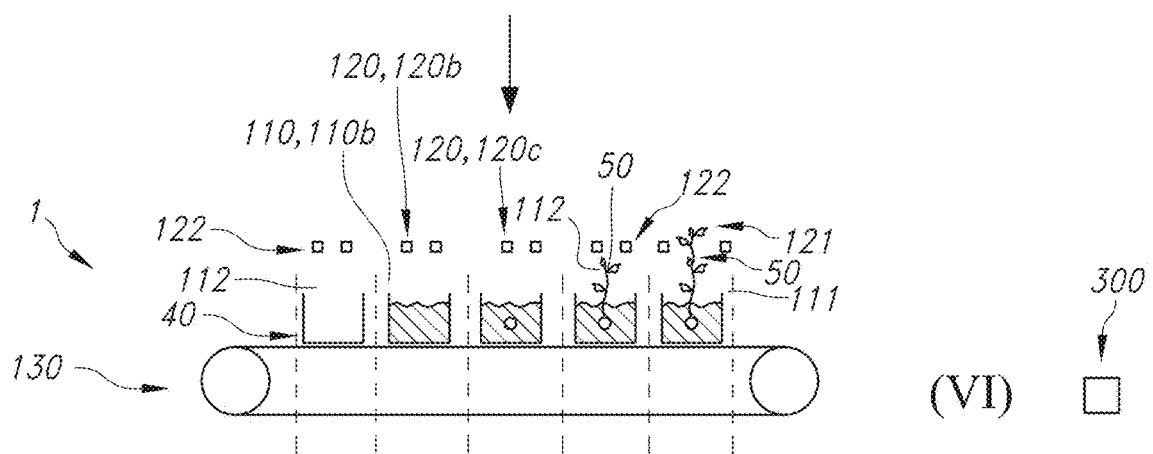

FIG. 1a-1b schematically depict an embodiment of the horticulture system 1 but in fact at the same time FIG. 1a-1b schematically depict some aspects of the method for determining plant-related parameter data of a plant 50.

FIG. 1a-1b schematically depict six phases, just by way of example, in which an embodiment of a horticulture system 1 could experience, especially when the horticulture system 1 comprises a transport element 130. The transport element 130 may be a conveyor belt, but other solutions may be chosen as well. Especially, the transport element 130 is configured to move a plant holder 40 sequentially through a series of the horticulture system units 100, more especially through the respective horticulture unit spaces 110. This series of horticulture system units 100 may at least including a first horticulture system unit comprising the first horticulture unit space.

As schematically depicted, the horticulture system 1 comprises a plurality of repeating horticulture system units 100 and a control system 300. Herein, by way of example there are five repeating horticulture system units 100. The respective horticulture system units 100 are indicated with references $100^a$, $100^b$, $100^c$, and $100^d$, and $100^e$. Each of the five repeating horticulture system units 100 comprises a horticulture unit space 110, indicated with the respective references $110^a$, $110^b$, $110^c$, $110^d$, and $110^e$, and respective radio transmission pairs, indicated with $120^a$, $120^b$, $120^c$, $120^d$, and $120^e$. As schematically depicted in FIG. 1a-1b, each horticulture system unit 100 has an (essentially) identical configuration of the (respective) radio transmission pair 120 relative to the (respective) horticulture unit space 110.

Further, by way of example the following is assumed, to further illustrate the invention. In the first phase (I), none of the horticulture system units 100 comprise an element. Or, one could say in this specific example that all horticulture system units 100 comprise essentially nothing, except for the transport element. For the sake of argument, we skip that latter aspect, as that aspect is not substantially different for the different horticulture system units 100. In the second phase (II), one of the horticulture system units 100 comprises an empty pot. Here, the pot is an example of the plant holder 40. In the third phase (III), the empty plant pot has been moved one stage further, and has been filled with substrate. The first from the left horticulture system unit 100 has again be provided with a new empty plant pot. In the fourth phase (IV), all existing plant pots have again been moved one step to the right. The first plant pot has now arrived in a third horticulture system unit 100, and has been provided with a seedling. Again, to the most left horticulture system unit 100 an empty plant pot has been provided. In the fifth phase (V), all existing plant pots have again been moved one step to the right. The first plant pot has now arrived in a fourth horticulture system unit 100, and a plant 50 has popped up. Again, to the most left horticulture system unit 100 an empty plant pot has been provided. In the sixth phase (VI), all existing plant pots have again been moved one step to the right. The first plant pot has now arrived in a fifth (and here last) horticulture system unit 100, and the plant 50 has grown to a larger plant 50. Again, to the most left horticulture system unit 100 an empty plant pot has been provided.

Especially, each horticulture system unit 100 comprises a horticulture unit space 110 and a radio transmission pair 120 arranged to monitor the horticulture unit space 110. The radio transmission pairs 120 are very schematically depicted as two small squares above in the respective horticulture unit spaces 110. However, they may also be arranged differently. The radio transmission pair 120 comprises a radio transmitter and a radio receiver arranged in radio signal receiving relationship.

Especially, the control system 300 is configured to execute in a unit sensing stage 230 a measurement in at least one of the horticulture unit spaces 110 with the respective radio transmission pair 120. The phrase "the control system 300 is configured to execute in a unit sensing stage 230 a measurement in at least one of the horticulture unit spaces 110 with the respective radio transmission pair 120" and similar phrases may especially refer to a kind of basic operation for which the horticulture system may at least be configured. It is a kind of basic action of operation, which may be executed for any of the horticulture unit spaces 110 at any time during processing. Depending upon the time, position, and use, such unit sensing stage 230. or unit sensing operation, may be used to generate a first signal, especially related to generating plant-related parameter data, and a second signal, especially related to generating a baseline signal, such as for a correction of the first signal.

Referring to FIG. 1b, e.g. the sixth phase VI, when one desires to determine plant related parameter data in relation to the plant 50 in the horticulture unit space 110', the unit sensing stage may be executed, which is (then) indicated as first signal sensing stage. A baseline measurement may be executed for one of the upstream positioned spaces $110^a$, $110^b$, $110^c$, and $110^d$, of which $110^e$ or $110^d$ may be most likely, because both include substrate and a seed/seedling or small plant, respectively. However, dependent upon the goal, also one of $110a$ or $110^b$ may be applied. It may even be possible to use the more than one of the upstream positioned spaces $110^a$, $110^b$, $110^c$, and $110^d$ to determine a baseline. Hence, when one desires to determine plant related parameter data in relation to the plant 50 in the horticulture unit space $110^e$, the unit sensing stage may be executed for this horticulture unit space $110^e$, which is (then) indicated as first signal sensing stage, and a unit sensing stage may be executed for one or more of the horticulture units spaces $110^a$, $110^b$, $110^c$, and $110^d$, which is (then) indicated as second signal sensing stage.

From the schematic drawing, it may also be clear that when measuring the plant+pot on the extreme right, i.e. $110^e$, one can use an earlier baseline, measured in an earlier stage. Alternatively or additionally, one can also use the baseline from any of the four units on the left, i.e. $100^a$, $100^b$, $100^c$, and $100^d$. This can be done at the same time as measuring the plant+pot on the extreme right, i.e. $110^e$. However, it may also be possible to measure the plant+pot on the extreme right, store the signal, and then measure the baseline from any of the four units on the left, and then process the data and arrive at the plant parameter-related parameter data.

Assume that one of the horticulture unit space 110 and the related radio transmission pair 120 are relevant for generating plant-related parameter, here in phase VI this may be the horticulture unit space 110' and the related radio transmission pair $120^e$, then the respective radio transmission pair, here radio transmission pair $120^e$, is herein also indicated as first radio transmission pair 121, as the first radio transmission pair is herein a radio transmission pair 120 used in the first signal sensing stage. Assume further that one of the other horticulture unit spaces 110 and the related radio transmission pair 120 are relevant for generating plant-related parameter, here in phase VI this may be the horticulture unit space $110^d$ and the related radio transmission pair $120^d$, then the respective radio transmission pair, here radio transmission pair $120^d$, is herein also indicated as second radio transmission pair 122, as the second radio transmission pair is herein a radio transmission pair 120 used in the second signal sensing stage.

Referring to this phase VI, in embodiments the control system 300 may be configured to execute in the operational mode the second signal sensing stage 232 (with the second radio transmission pair 122 for the second horticulture unit space 112), prior to the first signal sensing stage. However, in other embodiments the control system 300 may be configured to execute in the operational mode the second signal sensing stage 232 (with the second radio transmission pair 122 for the second horticulture unit space 112), simultaneously with the first signal sensing stage. As will be clear to a person skilled in the art, embodiments may also be combined. Further, when the first and second signal sensing stages are executed may depend upon the desired plant-related parameter data for one or more specific horticulture system units 100.

Hence, the control system 300 is further configured in an operational mode to: (a) execute a first signal sensing stage 231 (see FIGS. 1c and 1d), wherein the first signal sensing stage 231 (see FIGS. 1c and 1d) comprises the unit sensing stage 230 (see FIGS. 1c and 1d) with a first radio transmission pair 121 related to first horticulture unit space 111 (e.g.

hosting a plant 50) thereby providing a (related) first signal 241 to the control system 300; and (b) determine a plant-related parameter data based on the first signal 241 (see FIGS. 1c and 1d) and a baseline signal 245 (see FIGS. 1c and 1d), wherein the baseline signal 245 is based on a second signal 242 (see FIGS. 1c and 1d) obtained with an execution of a second signal sensing stage 232, wherein the second signal sensing stage 232 comprises the unit sensing stage 230 with a second radio transmission pair 122 related to a second horticulture unit space 112 thereby providing the (related) second signal 242.

As indicated above, "first" and "second" do not necessarily indicate a time relation. In general, a first signal sensing stage is executed after a (related) second signal sensing stage.

By way of example, referring to the second phase II in FIG. 1a, in embodiments the second horticulture unit space 112 does not contain the plant holder 40 during the second signal sensing stage 232 (see FIGS. 1c and 1d) with the second radio transmission pair 122 for the second horticulture unit space 112. Hence, in specific embodiments the second horticulture unit space 112 may be configured downstream of the first horticulture unit space 121 in the series of the horticulture system units 100. Further, in this example the second signal sensing stage 232 may be executed during the first signal sensing stage 231, but in principle also thereafter. In the latter embodiment, the first signal may be stored and processed after receipt of the second signal into plant-related parameter data.

By way of example, referring to the third phase III in FIG. 1a, in embodiments the second horticulture unit space 112 contains the plant holder 40 but does not contain a plant 50 during the second signal sensing stage 232 with the second radio transmission pair 122 for the second horticulture unit space 112). Hence, in specific embodiments the second horticulture unit space 112 may be configured upstream of the first horticulture unit space 121 in the series of the horticulture system units 100. However, as indicated above, this is not necessarily the case In specific embodiments, see also FIG. 2a, the control system 300 is further configured to control an environmental parameter of a plurality of the horticulture spaces 120, and to execute in the operational mode the second signal sensing stage 232 (with the second radio transmission pair 122 for the second horticulture unit space 112) while varying the environmental parameter.

In embodiments, the plant-related parameter data are volumetric plant-related parameter data selected from the group comprising a leaf volume, a root volume, and a fruit volume.

FIG. 1a-b also schematically depict an embodiments, or at least some aspects thereof, of a method for determining plant-related parameter data of a plant 50 in a horticulture system 1 comprising a plurality of repeating horticulture system units 100 and a control system 300. As indicated above, especially each horticulture system unit 100 comprises (i) a horticulture unit space 110 and (ii) a radio transmission pair 120 arranged to monitor the horticulture unit space 110. In embodiments, the radio transmission pair 120 comprises a radio transmitter and a radio receiver arranged in radio signal receiving relationship. Further, the control system 300 is configured to execute in a unit sensing stage 230 a measurement in at least one of the horticulture unit spaces 110 with the respective radio transmission pair 120.

Especially, the method comprises (a) executing a first signal sensing stage 231, wherein the first signal sensing stage 231 comprises the unit sensing stage 230 with a first radio transmission pair 121 for a first horticulture unit space 111 hosting a plant 50 thereby providing a (related) first signal 241 to the control system 300; and (b) determining a plant-related parameter data based on a the first signal 241 and b a baseline signal 245, wherein the baseline signal 245 is based on a second signal 242 obtained with an execution of a second signal sensing stage 232, wherein the second signal sensing stage 232 comprises the unit sensing stage 230 with a second radio transmission pair 122 related to a second horticulture unit space 112 thereby providing the (related) second signal 242.

In specific embodiments, the control system 300 may be configured to execute in the operational mode the second signal sensing stage 232 (with the second radio transmission pair 122 for the second horticulture unit space 112); wherein the method further comprises moving a plant holder 40 sequentially through a series of the horticulture system units 100 (especially including a first horticulture system unit comprising the first horticulture unit space); wherein the second horticulture unit space 112 is configured upstream of the first horticulture unit space 121 in the series of the horticulture system units 100; and wherein the plant-related parameter data are volumetric plant-related parameter data selected from the group comprising a leaf volume, a root volume, and a fruit volume.

Figure 2A:
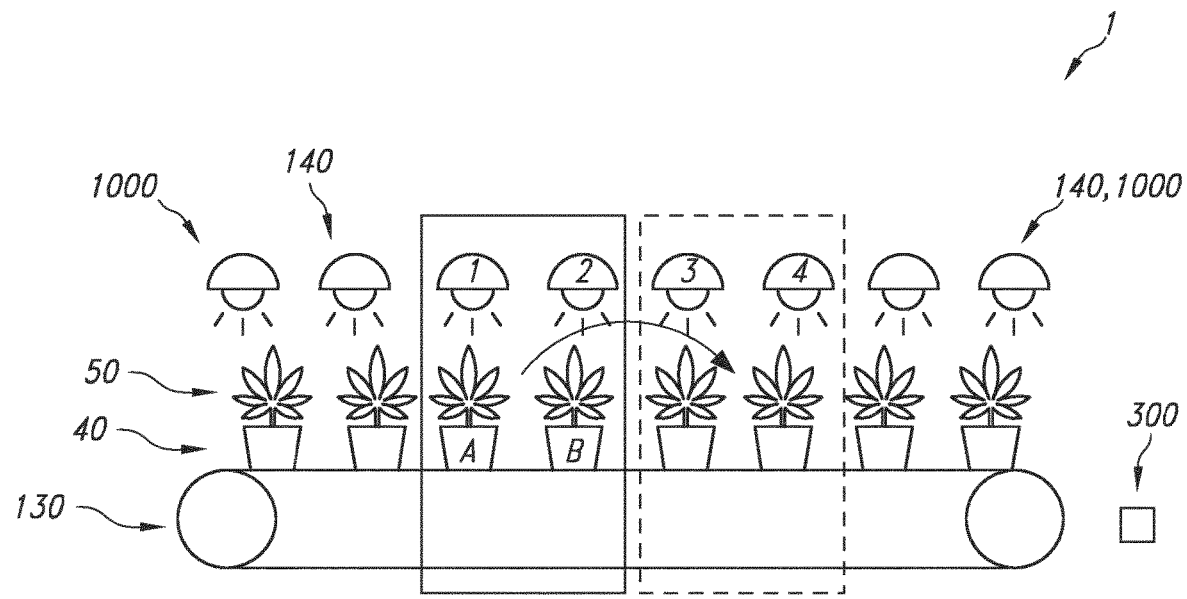
FIGS. 2a-2c schematically depict some further aspects of the invention. The schematic drawings are not necessarily to scale.

Further, in specific embodiments the horticulture system 1 may comprise one or more lighting devices 1000, wherein one or more of (a) the radio transmitters and (b) the radio receivers are integrated in the one or more lighting devices 1000 (see also FIG. 2a). Yet further, in specific embodiments the horticulture system 1 may comprises an actuator 140 selected from the group comprising a temperature control element, a plant trimmer, a water providing element, a nutrition supply element, a lighting device 1000, a disinfection device, an insect exposure element, and a harvesting element. Especially, in embodiments the control system 300 may be configured to control the actuator 140. Even more especially, the method may further comprise controlling the actuator 140 in dependence of the plant-related parameter data in relation to the first horticulture unit space 111.

Figure 1C:
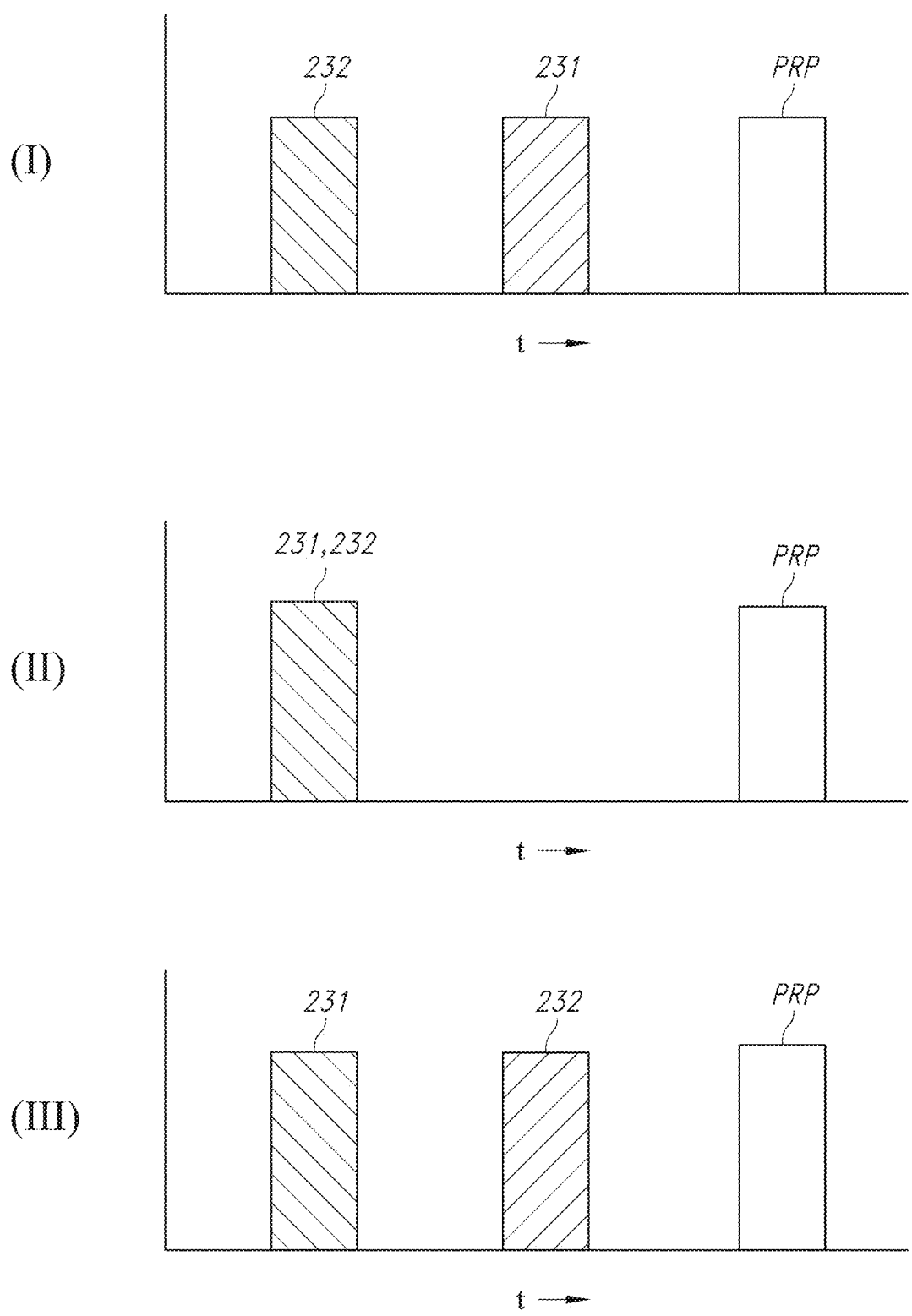

FIG. 1c schematically depicts three different embodiments of first signal sensing stage 231 and the second signal sensing stage 232.

In embodiment I, the second signal sensing stage 232 is executed earlier than the first signal sensing stage 231; based thereon plant-related parameter data PRP are generated. An example thereof is described in relation to sixth phase VI in FIG. 1b. Of course, this can also be described in relation to other phases and other embodiments.

In embodiment II, the second signal sensing stage 232 is executed simultaneously with the first signal sensing stage 231; based thereon plant-related parameter data PRP are generated. An example thereof is also described in relation to second phase II in FIG. 1a and/or sixth phase in FIG. 1b. Of course, this can also be described in relation to other phases and other embodiments.

In embodiment III, the second signal sensing stage 232 is executed later than the first signal sensing stage 231; based thereon plant-related parameter data PRP are generated. An example thereof is described in relation to second phase II in FIG. 1a. Of course, this can also be described in relation to other phases and other embodiments.

Hence, as indicated above the control system may be configured and/or the method may comprise (i) executing a first signal sensing stage 231, wherein the first signal sensing stage 231 comprises the unit sensing stage 230 with a first radio transmission pair 121 related to first horticulture unit space 111 (optionally hosting a plant 50) thereby providing a (related) first signal 241 to the control system 300; and (ii) determine a plant-related parameter data based on (a) the first signal 241 and (b) a baseline signal 245, wherein the baseline signal 245 is based on a second signal 242 obtained with an execution of a second signal sensing stage 232, wherein the second signal sensing stage 232 comprises the unit sensing stage 230 with a second radio transmission pair 122 related to a second horticulture unit space 112 thereby providing the (related) second signal 242

Figure 1D:
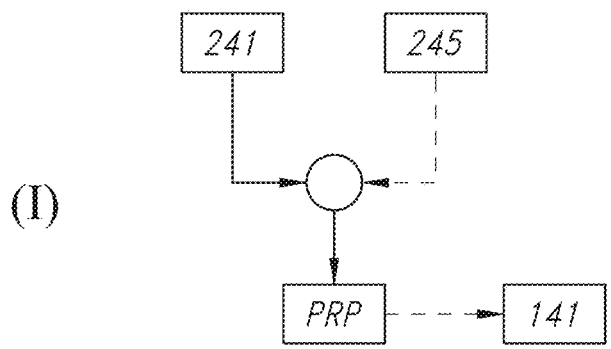
Figure 1D:
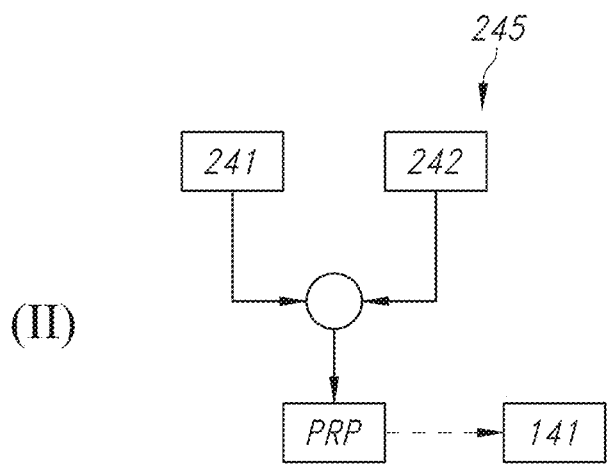
Figure 1D:
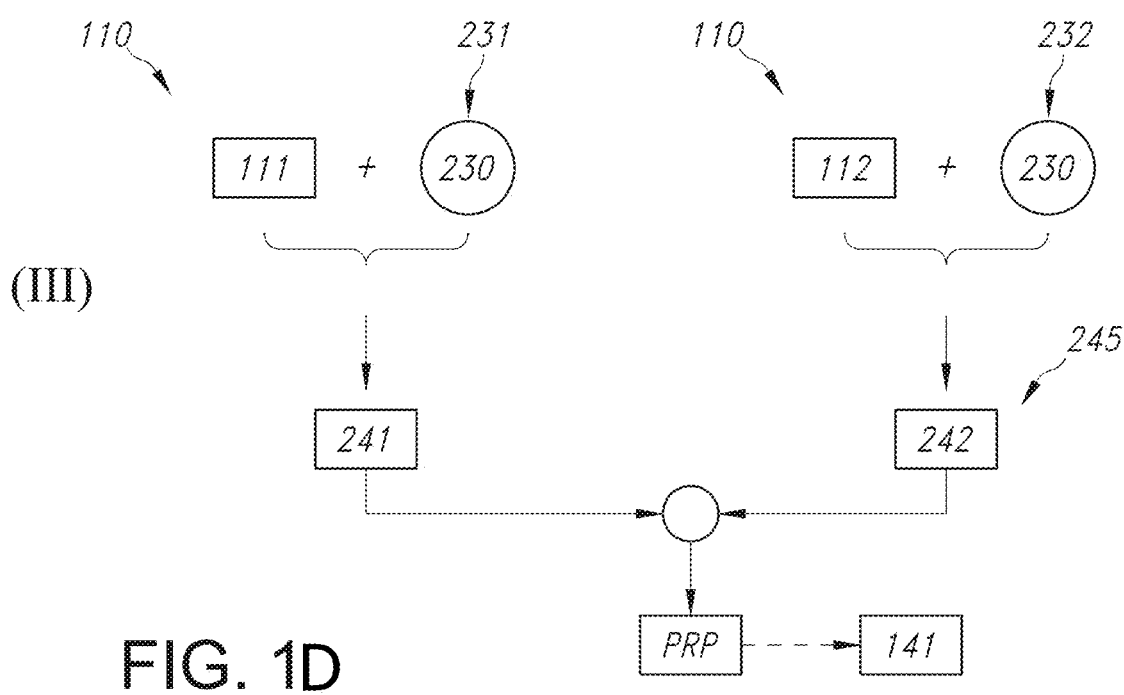

FIG. 1d very schematically depict a number of embodiments on how the plant-related parameter data, indicated with reference PRP, may be generated.

Embodiment I schematically depicts an embodiment wherein the baseline signal 245 is retrieved from a library. The plant-related parameter data PRP are determined on the basis of the first signal 241, obtained by executing the first signal sensing stage 231, and (b) a baseline signal 245.

Embodiment II schematically depicts an embodiment wherein the baseline signal 245 is obtained by executing the second signal sensing stage by which the second signal 242 is obtained. This second signal 242 may essentially be the baseline signal 245, or be at least derived therefrom. The plant-related parameter data PRP are determined on the basis of the first signal 241, obtained by executing the first signal sensing stage 231, and (b) a second signal 242.

Embodiment III very schematically depicts a possible way of executing the process or method (with e.g. the system as described herein). The sensing stage 230 is executed in relation to a first horticulture unit space 110, which is thereby indicated as first signal sensing stage 231 for first horticulture unit space 111. This generates the first signal 241. For instance, it is referred to the horticulture space 110' in phase VI of FIG. 1b. Here, the first horticulture unit space 111 includes a plant 50. Especially for reference purposes, the sensing stage 230 may also executed in relation to a second horticulture unit space 110, which is thereby indicated as second signal sensing stage 232 for second horticulture unit space 111. This generates the second signal 242. For instance, it is referred to the horticulture space 110' in phase VI of FIG. 1b. Here, the first horticulture unit space 111 includes a plant pot with only a seed(ling). The first signal 241 and the second signal 242 are processed into the plant-related parameter data PRP.

Hence, as indicated above the control system may be configured and/or the method may comprise (i) executing a first signal sensing stage 231, wherein the first signal sensing stage 231 comprises the unit sensing stage 230 with a first radio transmission pair 121 related to first horticulture unit space 111 (optionally hosting a plant 50) thereby providing a (related) first signal 241 to the control system 300; and (ii) determine a plant-related parameter data based on (a) the first signal 241 and (b) a baseline signal 245, wherein the baseline signal 245 is based on a second signal 242 obtained with an execution of a second signal sensing stage 232, wherein the second signal sensing stage 232 comprises the unit sensing stage 230 with a second radio transmission pair 122 related to a second horticulture unit space 112 thereby providing the (related) second signal 242.

Optionally, on the basis of the plant-related parameter data PRP an action may be executed. To this end, an actuator signal 141 may be generated, to have an actuator execute an action, or change an action, etc. (see further also below).

As indicated above, in modern greenhouses the horticulture plants may not be at static positions but may be (incrementally) moved (in a first-in-first-out approach) along a growth tray such as with a conveyor belt. Amongst others, this invention hence describes how to perform high-quality RF sensing for a plant, which has moved from a first position to a second position on e.g. the growing tray. Amongst others, it is herein described how to utilize the previously recorded baseline at the old position at the new position to ensure consistency and accuracy of the RF sensing. Other embodiments may include the timing when to record a baseline as well as diagnosing whether a sudden shift in baselines originates from a real micro-climate change at the tray or from faulty RF sensing baselines. In addition, it is herein described how the highly repetitive nature of greenhouses allows for stitching of RF sensing baselines.

It was experimentally found that using a high-quality baseline as input for the RF sensing algorithm is desirable for accurately estimating e.g. the leaf mass of the horticulture plants. As plants in modern growing facilities may no longer be static but move along e.g. a conveyor belt, it is challenging to create a high-quality baseline of the moved plant at each new location. It is herein described how to translate baselines recorded at a first position for usage as baselines for a second position. It appeared useful that in precision horticulture applications the timing of baselining may be optimized for RF sensing of e.g. leaf mass or fruit mass. Amongst others, a method is herein described, that when e.g. one RF sensing area reports a sudden change in the RF sensing signal, a smart comparison of baselines from adjacent areas can be used to distinguish a real microclimate change (e.g. locally increased humidity from a water leak) from faulty baselines just requiring re-baselining.

As indicated above, greenhouses are often highly automated; the position of a (group of) plant pots in a greenhouse is not static but the plants are over their lifetime (automatically) moved across many different positions in the greenhouse. It is hence desired that a first baseline generated during the plant's presence at a first position is subsequentially used to improve the RF sensing at a second position after the plant is moved.

In embodiments, horticulture plants take their baseline with them when moving to the next position on conveyor-belt based growing system. Many modern vertical farming facilities use a first-in-first-out (FIFO) automated logistics system, where young plants are inserted at one end into a growing layer and mature plants are extracted from the growing layer at the other end of the conveyor belt (see e.g. FIG. 2a). A first plant hence moves over time along the growing layer from a first position on the left side of the growing layer tray to a second position in the middle of the belt and afterwards to a third position at the right side of the belt. Whenever the first plant moves from the first position to the second position, a second new, younger plant is added to the growth layer belt at the first position. Initially, the first plant is monitored by a first and a second luminaire located to the left and right side of the first belt position. When the first plant has moved to the second position at the growing layer, the RF sensing of the first plant will be taken over by the third and a fourth luminaire. Hence, as the first pot gradually moves over time through the growing layer, many different pairs of lights will be assigned over time to perform RF sensing of the first pot over its entire lifetime in the greenhouse. We propose that the RF sensing baseline created by the first and second luminaire is re-used—after the first pot has moved to the second position—for the RF sensing performed by the third and fourth luminaire.

Optionally, partially overlapping RF sensing zones may be applied; while the first and second luminaire form the first sensing zone, the second luminaire is also used together with the third luminaire to form the second sensing zone.

Plant pots may be directly positioned on belts or may be configured in trays which are transported by belts.

FIG. 2a schematically depict an embodiments wherein the radio transmission pairs 120 are incorporated in luminaires 1000.

Hence, in embodiments the horticulture system 1 may comprise one or more lighting devices 1000, wherein one or more of the radio transmitters and the radio receivers are integrated in the one or more lighting devices 1000.

Note that the one or more of the radio transmitters and the radio receivers are not necessarily integrated lighting devices 1000, but can also be separately available, or be incorporated in other devices, or a combination of two or more of these. Herein, in this schematically depicted embodiments, the lighting devices 1000, such as luminaires, provide the function of lighting devices, one or more of the radio transmitters and the radio receivers, and actuator 140, as the lighting devices can be used as actuators by providing the light. As indicated above, actuation with a lighting device may include controlling the spectral power distribution and/or controlling the intensity.

In specific embodiments, see also FIG. 2a the control system 300 is further configured to control an environmental parameter of a plurality of the horticulture spaces, and to execute in the operational mode the second signal sensing stage (with the second radio transmission pair for the second horticulture unit space) while varying the environmental parameter. In specific embodiments the environmental parameter is selected from the group comprising a temperature, a substrate humidity, a leaf humidity, a relative humidity, an absolute humidity, an airflow, a density of the horticulture growth medium and a lighting parameter. However, other parameters may also be possible (see also above).

Hence, in embodiments, the horticulture system 1 comprises an actuator 140 selected from the group comprising a temperature control element, a plant trimmer, a water providing element, a nutrition supply element, a plant treatment supply element, a growth inhibitor supply element, a lighting device 1000, a disinfection device, an insect exposure element, and a harvesting element, wherein the control system 300 controls the actuator 140. Especially, during the operational mode the control system 300 operates the actuator 140 in dependence of the (determined value of the) plant-related parameter data, especially wherein the control system 300 operates the actuator 140 in relation to the first horticulture unit space.

FIG. 2a schematically depicts how plant A and B are gradually moved along the conveyor belt during their growth. At first, both plants are assessed with RF sensing by luminaires 1 and 2. After the plants A and plant B have moved by two pot positions along the conveyor belt, luminaires 3 and 4 take over the RF sensing of the two plants.

FIG. 2a also schematically depicts an embodiment wherein e.g. for an accurate handover of the RF sensing baseline from the first segment on the conveyor belt location to the second segment, it is required to first determine the RF sensing offset between the first segment (luminaires 1 and 2) and the second segment (luminaire 3 and 4). during this null-measurement of the baseline no plant mass is present. Note that the term segment indicates a horticulture unit space.

When translating the first baseline recorded at a first segment to second segment on the conveyor belt, it is required to calibrate and correct the target baseline for the second segment (see FIG. 2a). This calibration step is required as each RF sensing luminaire node-pair has certain characteristics with respect to the RF link signal. During a null-measurement (no-plants, only empty pots & soil), we set a first null baseline for the first segment and a second null baseline for the second segment. We then calculate an offset in the null-state between the first segment and the second segment and subsequentially utilize the determined null offset as correction factor when real baselines (i.e. with plants being present) are handed over between different segments.

The method outlined above may comprise three steps. As first step, the null baselines have to be established for first position (FP), second position (SP) and third position (TP) without plants present yet in the tray. We call the baselines BFP0 (Baseline First Position Null), BSP0 (Baseline Second Position Null) and BTP0 (Baseline Third Position Null). A second step is to calculate the correction-factors for each of the RF sensors in the baselines BSP0 and BTP0, assuming baseline BFP0 (which is the position where the youngest plant age will be inserted in the conveyor belt) is the reference. Assuming that each of the positions utilize 4 RF sensors each (i.e. a single RF sensing segment consists of 4 wireless luminaires, for instance two top lighting and two side lighting luminaires), there will be a correction-factor for each of the RF sensor per position:
  BSP0_CorrFactorRFsensor1,
   BSP0_CorrFactorRFsensor2,
   BSP0_CorrFactorRFsensor3,
   BSP0_CorrFactorRFsensor4
  BTP0_CorrFactorRFsensor1,
   BTP0_CorrFactorRFsensor2,
   BTP0_CorrFactorRFsensor3,
   BTP0_CorrFactorRFsensor4

The correction-factor may be calculated based on signal-quality characteristics within its position, compared with the signal-strength characteristics of the first position.

A third step is executed when the plant-under-growth is moved to a new tray position; the actual baseline for first position (BFPA=Baseline First Position Actual) and the actual baseline for second position (BSPA=Baseline Second Position Actual) are handed over to the next conveyor belt position every time after the conveyor belt moves by one plant pot. Each baseline handover includes baseline info of each of the RF sensors:
  BFPA==>BSP. New baseline for BSP: BFPA+ (BSP_CorrFactorRFsensor1,2,3,4)
  BSPA==>BTP. New baseline for BTP: BSPA+ (BTP_CorrFactorRFsensor1,2,3,4)

Optionally, an additional step may be used which looks at the actual baseline info to check if a baseline adaptation is required; the adaption is required in case of changing trends or unexpected variations in the baselines. The additional step may be done ahead of the step 2 described above to check whether to spend time/resources on correcting the baseline.

In a real-life greenhouse, some of the plants will be also located near the edge of the growing tray and hence will need to be treated differently in order to ensure optimal RF sensing performance:
  The plant pot that was before the move of the conveyor belt in the first position of the growing tray will have after the move a new (=younger) plant on its left side which was previously not there, and the new plant will interfere on RF Sensing due to additional absorption caused by its leaves, etc. To eliminate this issue, it may be advantageous to altogether omit the youngest plants located at the edge of the growing tray in the RF sensing measurement setup.

Similarly, the pot that was until the move in the before-to-last position on the conveyor belt will after the move of the conveyor belt suddenly no longer have a plant next to it (as the older neighbor plant was taken out from the conveyor belt). This means that a possible source of interference has disappeared and therefore the RF sensing signals might again look different.

Within a sufficiently long and homogeneous tray (i.e. away from the edges), there should not be significant differences once all pots have moved to their new position and hence the baseline from the previous location can be re-used.

The first and second segment on the conveyor belt plant tray only should share a RF sensing baseline if the surrounding greenhouse infrastructure is similar. For instance, if the first pair of growing lights at the first location is close to a (filled) water pipe and the second pair of growing lights at the second location has no water pipe in its vicinity, this physical difference in the surroundings will disturb the respective baselines.

In second embodiments, an optimal timing when to determine the RF sensing baseline is described. In embodiments, one may select at which state of the horticulture growing tray to perform the baselining (e.g. dry growing medium) and which states to avoid (e.g. just watered soil). For instance, right after watering of the soil may be a less suited state for determining the leaf mass with RF sensing, as the amount of applied water to the plant will greatly vary from irrigation time to irrigation time and hence no stable baseline for the RF sensing is available; on the other hand, if the soil is most dry (i.e. just before the next watering event), the soil will have least influence on the RF sensing and hence the plant mass will be the dominant contributor to the absorption of the wireless signals between the two growth lights performing the RS sensing.

In a third embodiments, attention is paid to greenhouses where the plants stay spatially static on the same growing tray, assign first set of luminaires at first location to record a baseline and then perform RF sensing with a second set of luminaires at a second location using that first baseline. Horticulture lights and plants may be spatially arranged in a highly repetitive environment. Hence, in principle a first pair of growing lights and a second pair of growing lights which are both located roughly in the middle of the (same) growth tray may both utilize the same baseline. This baseline sharing however may require that the RF sensing characteristics of the first and second pair are comparable. We hence propose to determine whether the steady state performance of the first and second pairs of lights are comparable and hence making them suitable for re-using the baseline info of the first RF sensing pair for the for second RF sensing pair or vice versa. For instance, the signal strength utilized by RF sensing depends on the position and orientation of antenna; hence if the antenna position of the first and second pair of growth lights are different, this will result in different RSSI data even if all the plants are identical. Hence, in this case the first and second pair are not suited for re-using of each other's baseline. The first pair and second RF sensing pair may also exchange insights on their respective "steady state" status e.g. do the plants have dry soil before watering? In general, sharing the baseline is especially advantageous whenever the sub-segments of the tray are at the moment in similar current "steady state", for instance both the first and second plant segments have dry soil (just before watering). In addition, for sharing baselines, the spatial arrangement of wireless lights, greenhouse infrastructure and pots should be preferably as similar as possible between the two different segments. Similarly, the plant's growth stage in the first and second area may have to be comparable (i.e. sharing a baseline between a freshly planted seedling vs ready-to-harvest plants will yield poor accuracy if the main purpose of RF sensing is leaf-mass estimation). However, if the grower is mostly interested in monitoring not in leaf-mass but in the rough uniformity of the drip-irrigation, the same baseline can also be shared between the first and second area, even if the respective plant growth stage is different.

In fourth embodiments, embodiments of a composite baseline stitched from contributions from two different RF sensing zones is discussed. For horticulture applications all growing trays or pots, etc., may essentially be equal, and the wireless luminaires are placed in a repetitive manner. In addition, with exception of the trays located at the very edge of the growing layer, all trays are surrounded by other identical trays. This makes it possible for horticulture to use composite baselines.

Figure 2B:
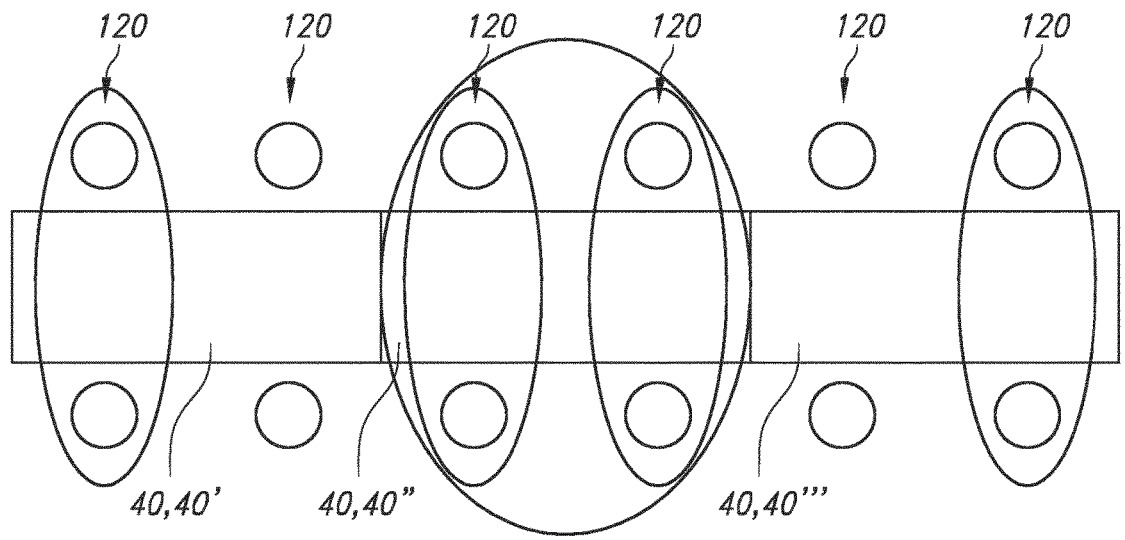
Figure 2B:
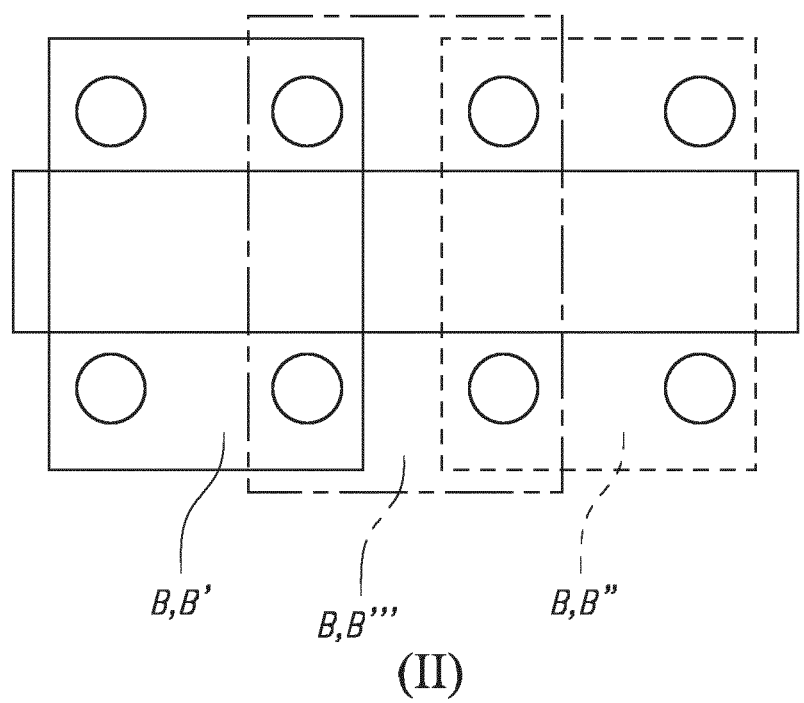

A composite baseline may be compiled as follows (see FIG. 2b, embodiment I): Baseline1 may be created by the most left set of lights of plant support 40 (indicated with reference 40'), such as a tray; baseline2 is created by the most-right set of lights of plant support 40 (indicated with reference 40"), such as a tray. Hence, plant support 40' and plant support 40" use differently positioned sets of lights (most-left on the tray vs most-right on the tray). Subsequently baseline3 for plant support 40 (indicated with reference 40'''), such as a tray, is created by calculating the composite using baseline1 from plant support 40 (indicated with reference 40'), such as a tray, and baseline2 from plant support 40 (indicated with reference 40"), such as a tray. Hence, FIG. 2b schematically depicts an embodiment wherein a (third) baseline is generated by stitching baselines 1 and 2. Hence, a baseline signal may be a composite baseline signal.

In fifth embodiments, embodiments of using past baselines recorded during earlier growing cycles of the same plant type at the same growing tray position is described. In horticulture growth facilities, the same plant growth trajectory is repeated over and over in time after each harvest with new plants taking the same old space. Hence, a RF sensing baseline may also utilize historic data from previous plant growth cycles (or earlier growth stages of the current growth cycle). For instance, the RF sensing baseline of the plant pots of week 1 (plant just seeded; no leaves yet) may be utilized in week 4 to determine the plant biomass by subtracting from the RF sensing signal in week 4 the RF sensing base line due to the plant pots from week 1.

In sixth embodiments, embodiments including recording a new baseline whenever the plant is altered by harvest chopping or re-arranging of the stems is described. New base lines may be created after the grower may have taken certain actions altering the biomass of the plant; for instance, a tomato grower may lower the tomato plant once every week so that tomato fruits are located on the bottom of the plant and new flowers are on top of the plant. For other plants such as cannabis, the plant is during its growth getting regularly chopped (leaves are removed).

In seventh embodiments, record the Plant-free baseline (with soil & pot only; no leaf biomass) at a different location than the current Plant-Under-Test is described. Amongst others, in embodiments it is herein proposed that the RF sensing for plant mass determines a plant-free baseline from a similarly spatial arrangement of lights/plant plots. In this method a first and second wireless horticulture luminaire form a first RF sensing detection zone and record a first RF sensing measurement (the null-baseline) at a first location housing with only plant pots filled with soil; however the plant pots at this first location have no tulip bulb or plant leaves/stem in it. A third and fourth wireless horticulture luminaire form a second RF sensing detection zone and record a second RF sensing measurement at a second location having the pot & soil with the actual "Plant Under Test" growing in the pot. Subsequently, we compare the RF sensing measurement from the second location (i.e. pot AND plant biomass present) with the plant-free null-baseline concurrently recorded at the first location. The advantage of the concurrent approach is that both the null measurement and the plant measurement share the same environment (humidity and temperature). The null-baseline measurement may be taken at the very beginning of the conveyor belt where the plant growth is still insignificant. Based on the difference between the null-measurement, our AI-enabled RF sensing algorithm can determine the current average density of a leaf canopy on a horticulture growth tray.

In eights embodiments, e.g. obsolete RF sensing baselines after watering rate of trickle irrigation is changed and initiate creation of a new baseline is described. New baselines could also be created as a function of expected/dynamic changes in control parameters of the growth. For example, if the growing system determines that due to growth conditions a different irrigation & nutrient rate is needed, the RF sensing system could choose to discard some of the old baselines, generate new ones right after the nutrient change, etc. For instance, if the grower determines that a higher concentration of fertilizer in the irrigation is needed, the higher fertilizer content in the soil might impact the baselines. Therefore, if the rate of fertilizer application is changed, the RF sensing system should be notified and use this trigger to discard the old RF sensing baselines as obsolete.

In ninths embodiments, embodiments creating multiple baselines representing different temperature, humidity and airflow, etc., is described. Temperature appears to impact the RF performance of nodes. Hence, a baseline recorded at a different previous ambient temperature in the greenhouse might not be suitable if the ambient temperature may have changed for instance due to issues with the climate control system or extreme weather. Additionally, before taking re-baselining actions, the system might assess the expected duration of the changes in these environmental parameters. A sudden temperature step might change due to workers/equipment being active in a section of the greenhouse (e.g. repairs disabling some equipment) and hence creating some changes to the micro-climate, but the worker will be eventually leaving the area and not having a lasting effect on temperature; hence no re-baselining is required. On the other hand, plants which are closer to adaptive ventilation ducts, doors, etc. might have more day-to-day variations and should therefore prepare to re-baseline more frequently. Humidity may attenuate wireless signals and that high relative humidity in the air—as typically the case in a greenhouse—reduces the RSSI. It is known that RSSI and Relative Humidity rises and falls together. For instance, prior art shows that relative Humidity may have a very high positive correlation (0.95) with RSSI at 2.4 GHz ZigBee while Absolute Humidity and RSSI are uncorrelated. Hence, due to the humidity dependency of RF sensing, we propose to record several RF sensing baselines representative of different humidity levels; when the humidity level within the greenhouse/leaf canopy may have changed, a new appropriate baseline recorded at similar humidity will be selected. These humidity-dependent baselines are especially important for future RF sensing systems utilizing 60 Hz Wi-Fi (Note: humidity effects will become more pronounced for RF sensing over the next 20 years as the higher the wireless frequency gets, the greater the attenuation due to hydrometeors (rain, cloud, fog, snow) will be). Hence, a baseline signal may be a composite baseline signal In tenths embodiments, recording a baseline with flower heads closed during night is described. Amongst others, it is herein proposes that multiple baselines will be recorded under different states of the horticulture plant. For instance, when growing horticulture flowers (e.g. Tulips), a baseline may be deliberately recorded when the flower head is closed in the night; after the flower may have opened up in the morning, the RF sensing measurement is performed which makes use of the baseline determined during the night. E.g. a Tulip may have a high relative proportion of flower compared to stem/leaves. Hence, the opening or closing of the flower will result in significant differences on the RSSI/CSI of the RF sensing signal, which can be used to successfully determine the open/close state of the flowers as well as estimating the amount/integral size/maturity of the flowers. If the RF sensing measurement shows little difference in RF sensing signals between the open and closed states of the Tulip flowers, this might indicate that the flowers for some reason have today not opened up fully in the morning; this can be an indication of some disease/fungus or abnormalities in irrigation and climate control system.

Figure 2C:
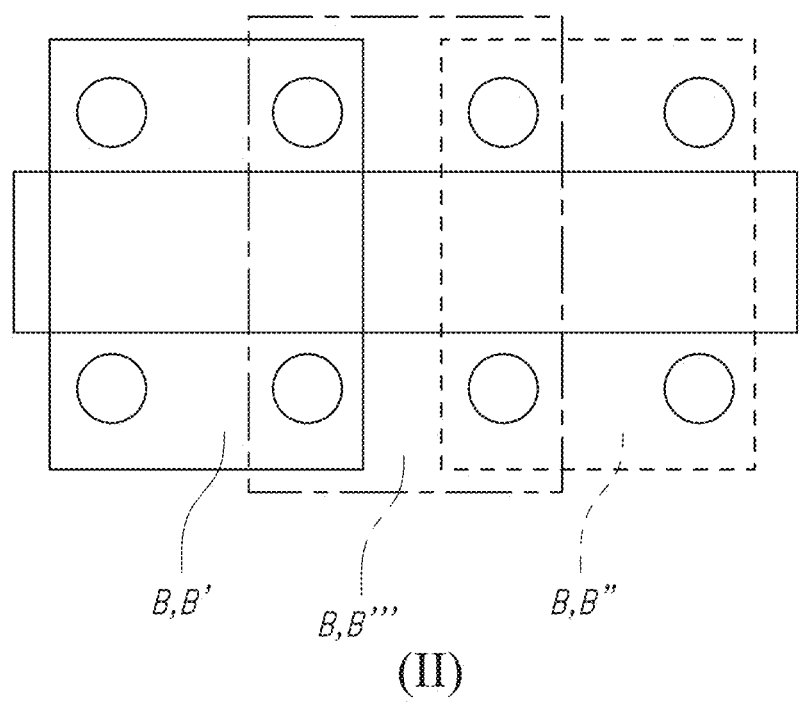

In eleventhsembodiments, embodiments including redefining RF sensing zones dynamically to diagnose microclimate changes with RF sensing (or identify that one of the baselines is faulty and trigger a re-baselining). A spatially highly repetitive growing tray may use a first and second RF sensing groups (see FIG. 2c, embodiment II), whereby the first and second sensing groups cover non-overlapping but adjacent areas. This embodiment describes how to diagnose the root-cause as well as determining the need for re-baselining IF the first and second RF sensing zone suddenly show significant differences between their respective RF sensing baselines while all measurable environmental parameters known to the control system at macro-level are equal (e.g. HVAC system sensor data). FIG. 2c, embodiments II, schematically depicts a spatial distribution of 8 horticulture growth lights seen from above.

Baseline B' and B" are expected to be equal due to repetitiveness of the growing tray and the same plant species under test and the same stage of plant growth. However, if we notice that the baseline B' and baseline B" suddenly become different with respect to each other, then we create a new baseline B''' which is comprised by the subset of lights from the "disagreeing" group B' and group B" which are most adjacent to each other.

In a first scenario: if the Baseline B''' exhibits a behavior that is somehow intermediate of what Baseline B' and Baseline B" showed, then there is a real environmental effect or event taking place (e.g. climate variations at microlevel due improper flow of air, water condensation, water accumulation, etc.). As a real effect is taking place, no recalibration of the baselines is required. In other words, due to the overlapping of baselines it should be expected that microclimates still have a noticeable impact on the adjacent, overlapping area. Therefore, a gradual change in baselines as we choose lights farther and farther away from the source location of the issue is indicative of a real microclimate change In a second scenario: However, if Baseline B''' shows a behavior very similar to either Baseline B' or Baseline B", then it means that respectively Baseline B" or Baseline B' were not properly selected, is outdated or needs baseline recalibration as due to the repetitiveness of the layout it is expected that under normal conditions all baselines will match. The baseline that stands out is therefore the one that is faulty or needs re-calibration The term "plurality" refers to two or more.

The terms "substantially" or "essentially" herein, and similar terms, will be understood by the person skilled in the art. The terms "substantially" or "essentially" may also include embodiments with "entirely", "completely", "all", etc. Hence, in embodiments the adjective substantially or essentially may also be removed. Where applicable, the term "substantially" or the term "essentially" may also relate to 90% or higher, such as 95% or higher, especially 99% or higher, even more especially 99.5% or higher, including 100%.

The term "comprise" also includes embodiments wherein the term "comprises" means "consists of".

The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices, apparatus, or systems may herein amongst others be described during operation. As will be clear to the person skilled in the art, the invention is not limited to methods of operation, or devices, apparatus, or systems in operation.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim.

Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The article "a" or "an" preceding an element does not exclude the presence of a plurality of such elements.

The invention may be implemented by means of hardware comprising several distinct elements, and by means of a suitably programmed computer. In a device claim, or an apparatus claim, or a system claim, enumerating several means, several of these means may be embodied by one and the same item of hardware. The mere fact that certain measures are recited in mutually different dependent claims does not indicate that a combination of these measures cannot be used to advantage.

The invention also provides a control system that may control the device, apparatus, or system, or that may execute the herein described method or process. Yet further, the invention also provides a computer program product, when running on a computer which is functionally coupled to or comprised by the device, apparatus, or system, controls one or more controllable elements of such device, apparatus, or system.

The invention further applies to a device, apparatus, or system comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A horticulture system comprising a plurality of horticulture system units for growing plants in growth stages and a control system, wherein:

each horticulture system unit comprises (i) a horticulture unit space comprising a plant at a respective growth stage and (ii) a radio transmission pair arranged to monitor the horticulture unit space with radio frequency sensing, wherein the radio transmission pair comprises a radio transmitter and a radio receiver arranged in radio signal receiving relationship;

the control system is configured to execute in a unit sensing stage a measurement in at least one of the horticulture unit spaces with the respective radio transmission pair;

the control system is configured in an operational mode to:

determine a first null baseline for a first horticulture system unit and a second null baseline for a second horticulture system unit;

calculate a null offset between the first and second null baselines;

execute a first signal sensing stage, wherein the first signal sensing stage comprises the unit sensing stage with a first radio transmission pair related to a first horticulture unit space of the first horticulture system unit thereby providing a first signal to the control system;

execute a second signal sensing stage, wherein the second signal sensing stage comprises the unit sensing stage with a second radio transmission pair related to a second horticulture unit space of the second horticulture system unit, thereby providing a second signal to the control system;

derive a baseline signal from the second signal obtained with the execution of the second signal sensing stage;

calibrate the baseline signal using the null offset as correction factor; and determine a volumetric plant-related parameter data of the plant in the first horticulture space based on
(a) the first signal and
(b) the baseline signal, wherein the volumetric plant-related parameter data is selected from the group comprising a leaf volume, a root volume, and a fruit volume;

wherein the plant comprised by the second horticulture unit space is at an earlier growth stage relative to the growth stage of the plant comprised by the first horticulture unit space.

2. The horticulture system unit according to claim 1, wherein the control system is configured to execute in the operational mode the second signal sensing stage, prior to the first signal sensing stage.

3. The horticulture system unit according to claim 1, wherein the control system is configured to execute in the operational mode the second signal sensing stage, simultaneously with the first signal sensing stage.

4. The horticulture system according to claim 1, wherein each horticulture system unit has an identical configuration of the radio transmission pair relative to the horticulture unit space.

5. The horticulture system according to claim 1, further comprising a transport element, wherein the transport element is configured to move a plant holder sequentially through a series of the horticulture unit spaces.

6. The horticulture system according to claim 1, wherein the control system is further configured to control an environmental parameter of a plurality of the horticulture spaces, and to execute in the operational mode the second signal sensing stage while varying the environmental parameter.

7. The horticulture system according to claim 6, wherein the environmental parameter is selected from the group comprising a temperature, a substrate humidity, a leaf humidity, a relative humidity, an absolute humidity, an airflow, a density of the horticulture growth medium and a lighting parameter.

8. The horticulture system according to claim 1, wherein the horticulture system comprises one or more lighting devices, wherein one or more of (a) the radio transmitters and (b) the radio receivers are integrated in the one or more lighting devices.

9. The horticulture system according to claim 1, wherein the horticulture system comprises an actuator selected from the group comprising a temperature control element, a plant trimmer, a water providing element, a nutrition supply element, a plant treatment supply element, a growth inhibitor supply element, a lighting device, a disinfection device, an insect exposure element, and a harvesting element, wherein the control system controls the actuator, and wherein during the operational mode the control system operates the actuator in dependence of the plant-related parameter data.

10. The horticulture system according to claim 1, wherein said radio signal is indicative of a control command arranged for controlling an electrical device.

11. A method for determining a volumetric plant-related parameter data of a plant in a horticulture system comprising a plurality of repeating horticulture system units and a control system; wherein the volumetric plant-related parameter data is selected from the group comprising a leaf volume, a root volume, and a fruit volume;
wherein: (a) each horticulture system unit comprises (i) a horticulture unit space and (ii) a radio transmission pair arranged to monitor the horticulture unit space with radio frequency sensing, wherein the radio transmission pair comprises a radio transmitter and a radio receiver arranged in radio signal receiving relationship; and (b) the control system is configured to execute in a unit sensing stage a measurement in at least one of the horticulture unit spaces with the respective radio transmission pair; and wherein the method comprises:

determining first null baseline for the first horticulture system unit and a second null baseline for the second horticulture system unit;

calculating a null offset between the first and second null baselines;

executing a first signal sensing stage, wherein the first signal sensing stage comprises the unit sensing stage with a first radio transmission pair related to a first horticulture unit space of the first horticulture system unit hosting a plant at a respective growth stage thereby providing a first signal to the control system;

executing a second signal sensing stage, wherein the second signal sensing stage comprises the unit sensing stage with a second radio transmission pair related to a second horticulture unit space of the second horticulture system unit hosting a plant at a respective growth stage thereby providing a second signal to the control system;

deriving a baseline signal from the second signal obtained with the execution of the second signal sensing stage;

calibrating the baseline signal using the null offset as correction factor; and determining a plant-related parameter data based on (a) the first signal and (b) the baseline signal;

wherein the plant comprised by the second horticulture unit space is at an earlier growth stage relative to the growth stage of the plant comprised by the first horticulture unit space.

12. The method according to claim 11, wherein the method further comprises moving a plant holder sequentially through a series of the horticulture system units.

13. The method according to claim 11, wherein the horticulture system comprises one or more lighting devices, wherein one or more of (a) the radio transmitters and (b) the radio receivers are integrated in the one or more lighting devices; wherein the horticulture system (1) comprises an actuator selected from the group comprising a temperature control element, a plant trimmer, a water providing element, a nutrition supply element, a lighting device, a disinfection device, an insect exposure element, and a harvesting element, wherein the control system controls the actuator; and wherein the method further comprises controlling the actuator in dependence of the plant-related parameter data in relation to the first horticulture unit space.

* * * * *